United States Patent
Sinai et al.

(10) Patent No.: US 10,603,301 B2
(45) Date of Patent: Mar. 31, 2020

(54) CANNABIS-BASED EXTRACTS AND TOPICAL FORMULATIONS FOR USE IN SKIN DISORDERS

(71) Applicant: ONE WORLD CANNABIS LTD, Petach Tikva (IL)

(72) Inventors: Alon Sinai, Petach Tikva (IL); Ziv Turner, Petach Tikva (IL); Yehuda Baruch, Gedera (IL)

(73) Assignee: One World Cannabis LTD, Ramat Gan (IL)

( * ) Notice: Subject to any disclaimer, the term of this patent is extended or adjusted under 35 U.S.C. 154(b) by 11 days.

(21) Appl. No.: 15/629,230

(22) Filed: Jun. 21, 2017

(65) Prior Publication Data

US 2018/0042890 A1    Feb. 15, 2018

Related U.S. Application Data

(63) Continuation-in-part of application No. PCT/IL2015/051234, filed on Dec. 21, 2015.

(60) Provisional application No. 62/095,020, filed on Dec. 21, 2014.

(51) Int. Cl.

| | |
|---|---|
| *A61K 36/00* | (2006.01) |
| *A61K 31/352* | (2006.01) |
| *A61K 9/00* | (2006.01) |
| *A61K 45/06* | (2006.01) |
| *A61K 9/06* | (2006.01) |
| *A61K 31/05* | (2006.01) |
| *A61K 47/06* | (2006.01) |
| *A61K 47/10* | (2017.01) |
| *A61K 47/12* | (2006.01) |
| *A61K 47/14* | (2017.01) |
| *A61K 47/18* | (2017.01) |
| *A61K 47/22* | (2006.01) |
| *A61K 47/36* | (2006.01) |
| *A61K 47/46* | (2006.01) |
| *A61K 36/185* | (2006.01) |

(52) U.S. Cl.
CPC .......... *A61K 31/352* (2013.01); *A61K 9/0014* (2013.01); *A61K 9/06* (2013.01); *A61K 31/05* (2013.01); *A61K 45/06* (2013.01); *A61K 47/06* (2013.01); *A61K 47/10* (2013.01); *A61K 47/12* (2013.01); *A61K 47/14* (2013.01); *A61K 47/18* (2013.01); *A61K 47/183* (2013.01); *A61K 47/22* (2013.01); *A61K 47/36* (2013.01); *A61K 47/46* (2013.01); *A61K 36/185* (2013.01)

(58) Field of Classification Search
CPC ..................................................... A61K 36/00
USPC ......................................................... 424/725
See application file for complete search history.

(56) References Cited

U.S. PATENT DOCUMENTS

| | | |
|---|---|---|
| 2007/0032544 A1 | 2/2007 | Korthout et al. |
| 2008/0058426 A1 | 3/2008 | Muhammed et al. |
| 2008/0255224 A1 | 10/2008 | Blum |
| 2014/0298511 A1 | 10/2014 | Lewis et al. |
| 2017/0112855 A1 | 4/2017 | Modi |

FOREIGN PATENT DOCUMENTS

| | | |
|---|---|---|
| CN | 101099817 A | 1/2008 |
| CN | 102225143 A | 10/2011 |
| GB | 2542797 A | 4/2017 |
| WO | WO 2005/072719 A1 | 8/2005 |
| WO | 2016/103254 A1 | 6/2016 |

OTHER PUBLICATIONS

International Search Report (PCT/ISA/210) dated Mar. 31, 2016, by the Japanese Patent Office as the International Searching Authority for International Application No. PCT/ IL2015/051234.

Written Opinion (PCT/ISA/237) dated Mar. 31, 2016, by the Japanese Patent Office as the International Searching Authority for International Application No. PCT/IL2015/051234.

Wilkinson et al., Cannabinoids inhibit human keratinocyte proliferation through a non-CB1/CB2 mechanism and have a potential therapeutic value in the treatment of psoriasis, Journal of Dermatological Science, 45:87-92 (2007).

*Primary Examiner* — Michael V Meller
(74) *Attorney, Agent, or Firm* — Browdy and Neimark, PLLC

(57) ABSTRACT

The present invention discloses a pharmaceutical topical composition comprising cannabidiol (CBD) or a derivative thereof and Tetrahydrocannabinol (THC) or a derivative thereof in an about 1:1 ratio, useful for treatment or prevention of inflammatory skin disorders, and treatment methods thereof.

17 Claims, 8 Drawing Sheets

CANNABIS-BASED EXTRACTS AND TOPICAL FORMULATIONS FOR USE IN SKIN DISORDERS

FIELD OF THE INVENTION

The present disclosure relates to novel compositions and methods for treatment of skin conditions. More particularly the current invention pertains to a composition comprising Tetrahydrocannabinol (THC) and/or cannabidiol (CBD) or derivatives thereof for treating dermatologic conditions and especially inflammatory skin pathologies.

BACKGROUND OF THE INVENTION

Inflammatory skin diseases are a group of diseases that results in inflammation of the skin. These diseases are characterized by itchiness, red skin, and a rash. Psoriasis, also known as psoriasis vulgaris, is a chronic, inflammatory skin disease characterized by red, scaly patches, papules, and plaques, which usually itch. The skin lesions seen in psoriasis may vary in severity from minor localized patches to complete body coverage. The disease affects 2-4% of the general population.

The causes of psoriasis are not fully understood. It is not purely a skin disorder and can have a negative impact on many organ systems. Psoriasis is also associated with an increased risk of certain cancers, cardiovascular disease, and other immune-mediated disorders such as Crohn's disease and ulcerative colitis.

Psoriasis is generally considered a genetic disease, though it is triggered and influenced by environmental factors. Psoriasis characterized by accelerated growth of epidermis cells (keratinocyte cells) accompanied by an inflammation.

Conditions reported as accompanying a worsening of the disease include chronic infections, stress, changes in season and climate, scratching psoriasis skin lesions, skin dryness, excessive alcohol consumption, cigarette smoking, and obesity. People with advanced HIV/AIDS often exhibit psoriasis. Oxidative stress, stress, and withdrawal of a systemic corticosteroid have each been suggested as a trigger for psoriasis. Other drugs that may induce the disease include beta blockers, lithium, antimalarial medications, non-steroidal anti-inflammatory drugs, terbinafine, calcium channel blockers, captopril, glyburide, granulocyte colony-stimulating factor, interleukins, interferons, lipid-lowering drugs, and TNF inhibitors such as infliximab or adalimumab.

No cure is available for psoriasis, but various topical and systemic treatments can help control the symptoms. Topical agents are typically used for mild disease, phototherapy for moderate disease, and systemic agents for severe disease.

For topical treatment corticosteroid preparations are the most effective but also Vitamin D analogues such as paricalcitol were shown to be effective.

Psoriasis resistant to topical treatment and phototherapy may be treated with systemic therapies including oral medications or injectable treatments. Non-biologic systemic treatments frequently used for psoriasis include methotrexate, ciclosporin, hydroxycarbamide, fumarates such as dimethyl fumarate, and retinoids. Biologic systemic treatment includes drugs that target T cells are such as efalizumab and alefacept.

The use of cannabis in traditional medicine is dated back centuries ago as remedy for numerous pathologies. Among its medicinal properties, several extracts obtained from the herbs are known to possess anti-inflammatory capacity. However, only in recent years the therapeutic potential of cannabis, its chemical composition and mechanism of action are discovered. In addition, controlled studies are now being performed to standardize its use and transform the field by presenting evidence-based experiments.

Cannabinoids are a group of 21-carbon-containing terpenophenolic compounds produced by *Cannabis* species. Cannabinoids may also be synthetically produced. Cannabinoids have shown to inhibit keratinocyte proliferation which is induced in psoriasis. They also have shown anti-inflammatory properties that may be beneficial for treatment of psoriasis.

Several patent documents recite compositions for treating psoriasis which comprise cannabis either systematically or topically. For example, patent application CN101099817 recites a composition comprising cannabis as well as radix rehmanniae, radix salviae miltiorrhizae, figwort, dyers woad leaf, asiatic moonseed, cortex dictamni, rhizoma bistortae, forsythia, china root, saffron, long-noded pit viper and honeysuckle for treating psoriasis. Patent document CN102225143 recites the use of cannabis in a composition for topical use which comprises in addition to cannabis also sesame, black soya bean, peach kernel, apricot kernel, platycladi seed, bunge cherry seed, angelica sinensis, the root of bidentate achyranthes, cacumen biotae twig, sesame oil, frankincense, myrrh radix angelicae pubescentis, notopterygium root, golden cypress, coptis chinensis, cacumen biotae, radix sophorae flavescentis, schizonepeta, saposhnikovia divaricata, philippine violet herb, caulis polygoni multiflori, caulis spatholobi, platycodon grandiflorum, cortex dictamni, rhizoma cyperi and peony bark. However, none of the disclosed patent documents recite the use of specific extracted cannabinoids. In addition, they all recited a composition comprising over 10 ingredients.

In view of the above, It is still a long felt and unmet need for a naturally originated composition with minimal adverse effects that is specifically useful for treatment of inflammatory skin disorders such as psoriasis.

SUMMARY OF THE INVENTION

It is thus one object of the present invention to disclose a pharmaceutical topical composition comprising:
  a. a carrier formulation comprising at least two of:
     i. Glycerin;
     ii. Niacinamide;
     iii. Salicylic Acid; and
     iv. β-Caryophyllene; and
  b. *Cannabis* oil comprising cannabidiol (CBD) or a derivative thereof and Tetrahydrocannabinol (THC) or a derivative thereof in an about 1:1 ratio,
     wherein said composition provides a synergistic effect with respect to treatment of inflammatory skin conditions as compared to the effect provided by said carrier formulation or said *Cannabis* oil administered separately in similar concentrations.

It is a further object of the present invention to disclose the pharmaceutical topical composition as defined above, wherein said composition further comprises at least one ingredient selected from the group consisting of: Glyceryl Stearate & PEG-100 Stearate, Cetyl Alcohol, Allantoin, Butyrospermum Parkii, Petrolatum, Steareth-21, Tocopheryl Acetate, Lavandula Angustifolia oil, Xanthan Gum, Dipotassium Glycyrrhizate, Aloe Barbadensis Leaf Juice, Triethanolamine, Bisabolol, Disodium EDTA, vitamin B3, keratolytic agent, anti irritation agent, anti oxidant, terpene, cannabis terpene, anti skin redness agent, antiadherent, binder, coating, disintegrant, flavour, colour, lubricant, glidant, sorbent, preservative, filler, emulsifier, humectant, thickener, skin nourishing agent, skin moistening agent, occlusive agent, emollient agent, calming agent, natural smell agent, suspending agent, soothing agent, pH adjustment agent, complexant, purified water, Shea Butter, Lavender Oil, and any combination thereof.

It is a further object of the present invention to disclose the pharmaceutical topical composition as defined in any of the above, wherein the concentration of said CBD or said derivative thereof and said THC or a derivative thereof is about CBD:THC 3%:3%.

It is a further object of the present invention to disclose the pharmaceutical topical composition as defined in any of the above, wherein said composition comprises β-caryophyllene in about 0.5% concentration.

It is a further object of the present invention to disclose the pharmaceutical topical composition as defined in any of the above, wherein said composition comprises cannabis oil in about 10% concentration.

It is a further object of the present invention to disclose the pharmaceutical topical composition as defined in any of the above, wherein said composition reduces Lipopolysaccharide (LPS) and/or Epidermal Growth Factor (EFG) and/or TNFα induced hyperproliferation of skin cells ex vivo or in vitro.

It is a further object of the present invention to disclose the pharmaceutical topical composition as defined in any of the above, wherein said composition provides a synergistic effect with respect to at least one of: (a) inhibition of proliferation (b) inhibition of inflammation, as compared to the effect provided by said carrier formulation or said *Cannabis* oil administered separately in similar concentrations.

It is a further object of the present invention to disclose the pharmaceutical topical composition as defined in any of the above, wherein said composition provides a synergistic effect with respect to inhibition of cytokines secretion as compared to the effect provided by said carrier formulation or said *Cannabis* oil comprising said CBD or a derivative thereof and said THC or a derivative thereof administered separately in similar concentrations.

It is a further object of the present invention to disclose the pharmaceutical topical composition as defined in any of the above, wherein said cytokines are selected from the group consisting of: IL-8, IL-33 and any combination thereof.

It is a further object of the present invention to disclose the pharmaceutical topical composition as defined in any of the above, wherein said composition reduces epidermal turnover rate.

It is a further object of the present invention to disclose the pharmaceutical topical composition as defined in any of the above, wherein said composition provides a synergistic effect with respect to improvement of inflammatory skin disorders as compared to the effect provided by the THC or a derivative thereof or by the CBD or a derivative thereof, or their combination, or said carrier formulation, administered separately in a similar concentration.

It is a further object of the present invention to disclose the pharmaceutical topical composition as defined in any of the above, wherein said composition provides a synergistic effect with respect to improvement of inflammatory skin disorders as compared to the effect provided by said composition absent of said *Cannabis* oil and/or said β-caryophyllene.

It is a further object of the present invention to disclose the pharmaceutical topical composition as defined in any of the above, wherein said improvement of inflammatory skin disorders comprises an effect selected from the group consisting of: reduction of hyperproliferation, reduction of IL-8 secretion, reduction of IL-33 secretion, reduction of skin inflammation, reduction of epidermal turnover rate and any combination thereof.

It is a further object of the present invention to disclose the pharmaceutical topical composition as defined in any of the above, wherein said composition provides a synergistic effect with respect to treating symptoms of psoriasis selected from the group consisting of inhibition of cell proliferation, inhibition proinflammatory cytokine mediators in psoriasis, and a combination thereof.

It is a further object of the present invention to disclose the pharmaceutical topical composition as defined in any of the above, wherein said composition reduces inflammation characteristics of said skin in a comparable manner to a positive steroid control such as dexamethasone.

It is a further object of the present invention to disclose the pharmaceutical topical composition as defined in any of the above, wherein said composition provides a synergistic effect with respect to inhibition of skin hyperproliferation and of skin inflammation as compared to the effect provided by each of the carrier formulation components of (a) and/or each of the *Cannabis* oil components of (b) when administered separately in a similar concentration.

It is a further object of the present invention to disclose the pharmaceutical topical composition as defined in any of the above, wherein said composition is formulated in a dosage form selected from the group consisting of cream, ointment, lotion, foam, film, transdermal patch and any combination thereof.

It is a further object of the present invention to disclose the pharmaceutical topical composition as defined in any of the above, wherein said composition is administered in combination with an additional psoriasis therapeutic agent; said additional psoriasis therapeutic agent is selected from the group consisting of methotrexate, ciclosporin, hydroxycarbamide, fumarates, retinoids, efalizumab and alefacept, vitamin D and derivatives thereof and any combination thereof.

It is a further object of the present invention to disclose the pharmaceutical topical composition as defined in any of the above, wherein said composition combined with said at least one psoriasis therapeutic agent provides a synergistic or additive effect with respect to treating or preventing hyperproliferative or inflammatory skin conditions relative to the effect provided by said psoriasis therapeutic agent administered separately.

It is a further object of the present invention to disclose the pharmaceutical topical composition as defined in any of the above, wherein said composition is dissolved in a lipophilic solvent or suspension carrier selected from a group consisting of medium-chain triglyceride, short-chain triglyceride, medium-chain partial glyceride, polyoxyethylated fatty alcohol, polyoxyethylated fatty acid, polyoxyethylated fatty acid triglyceride or partial glyceride, ester of fatty acids with low molecular weight alcohols, a partial ester of sorbitan with fatty acids, a polyoxyethylated partial ester of sorbitan with fatty acids, a partial ester of sugars or oligomeric sugars with fatty acids, a polyethylene glycol, lecithin, vegetable oil, and any combination thereof.

It is a further object of the present invention to disclose a pharmaceutical topical composition comprising: (a) a carrier formulation comprising:
   i. Glyceryl Stearate & PEG-100 Stearate
   ii. Glycerin iii. Niacinamide
iv. Cetyl Alcohol
v. Salicylic Acid
vi. Allantoin
vii. Butyrospermum Parkii
viii. Petrolatum
ix. Steareth-21
x. Tocopheryl Acetate
xi. Lavandula Angustifolia oil
xii. Xanthan Gum
xiii. Dipotassium Glycyrrhizate
xiv. Aloe Barbadensis Leaf Juice
xv. Triethanolamine
xvi. Bisabolol
xvii. Disodium EDTA
xviii. β-Caryophyllene 0.5%
   (b) *Cannabis* oil comprising cannabidiol (CBD) or a derivative thereof and Tetrahydrocannabinol (THC) or a derivative thereof in an about 1:1 ratio, wherein said composition provides a synergistic effect with respect to treatment of, or inhibition of hyperproliferative and/or inflammatory skin conditions as compared to the effect provided by said carrier formulation or said *Cannabis* oil administered separately to said skin tissue in similar concentrations.

It is a further object of the present invention to disclose a method of treating or inhibiting hyperproliferative and/or inflammatory skin conditions in a subject, said method comprises steps of:
   a. providing a topical composition according to claim 1; and
   b. administering said composition to said subject topically at a therapeutically effective dosage.

It is a further object of the present invention to disclose the method as defined in any of the above, wherein said step (b) comprises at least one step selected from the group consisting of:
   a. administering said composition in a therapeutic dosage of up to about 1500 mg, preferably a dosage in the range of about 100 mg to about 1500 mg of said composition, more preferably a dosage of up to about 30 mg of said CBD, THC, about 5 mg β-caryophyllene and any combination thereof, per day;
   b. administering said composition in a therapeutic dosage of CBD of up to 100 mg per day, preferably in the range of about 10 mg to about 100 mg per day, more preferably in a dosage of up to about 30 mg per day;
   c. administering the composition in a dosage of THC of up to 100 mg per day, preferably in the range of about 10 mg to about 100 mg per day, more preferably in a dosage of up to about 30 mg per day; and
   d. administering the composition in a dosage of β-Caryophyllene of up to 100 mg per day, preferably in the range of about 3 mg to about 10 mg per day, more preferably in a dosage of up to about 5 mg per day.

DETAILED DESCRIPTION OF THE PREFERRED EMBODIMENTS

Figure 1A:
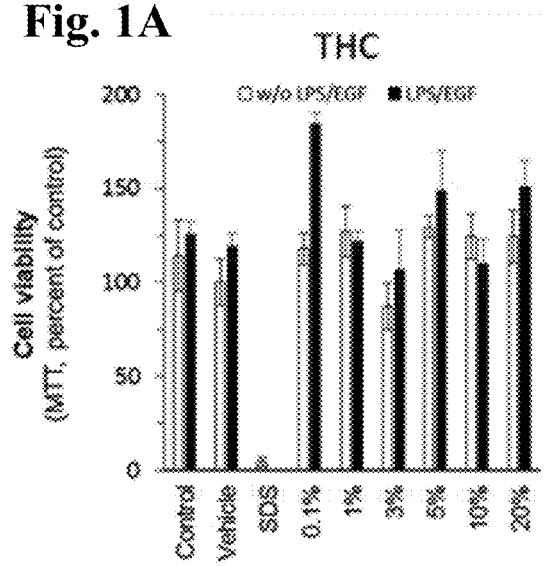
FIGS. 1A-1D illustrate a dose-response analysis, where the different Test items (Ethanol based extracts) were applied topically without or with LPS/EGF; After 48 hr incubation, epidermis viability was determined by MTT; Mean±SEM, n=3.
Figure 1B:
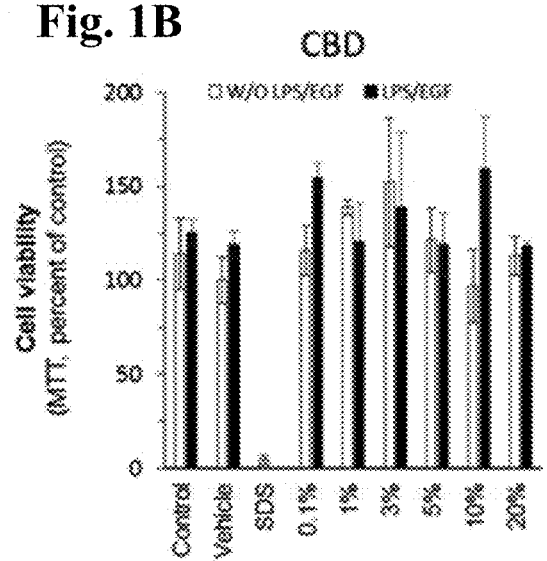
Figure 1C:
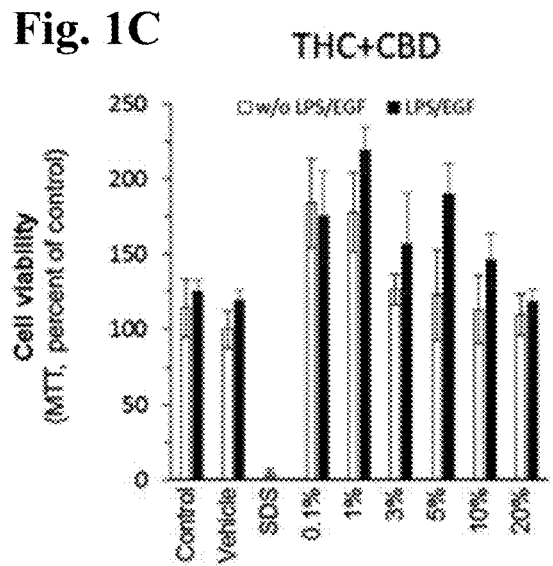
Figure 1D:
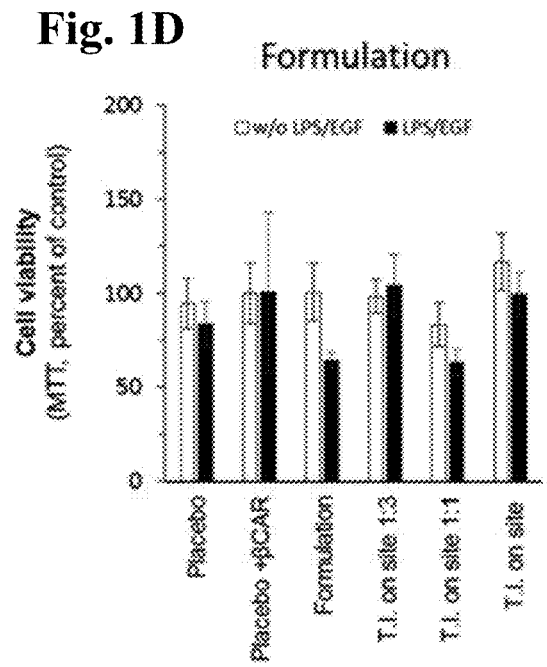

In the following detailed description of the preferred embodiments, reference is made to the accompanying drawings that form a part hereof, and in which are shown by way of illustration specific embodiments in which the invention may be practiced. It is understood that other embodiments may be utilized and structural changes may be made without departing from the scope of the present invention. The present invention may be practiced according to the claims without some or all of these specific details. For the purpose of clarity, technical material that is known in the technical fields related to the invention has not been described in detail so that the present invention is not unnecessarily obscured.

The essence of the present invention is to provide a composition for treating psoriasis comprising cannabidiol (CBD) and/or Tetrahydrocannabinol (THC) or an extract thereof and/or β-caryophyllene. More specifically the present invention recites a composition comprising cannabis extract for either topical or oral use.

The invention relates to a novel formulation containing *Cannabis* extracts for the treatment of inflammatory skin conditions, mainly psoriasis.

Psoriasis is a common, chronic and inflammatory skin disease for which there is no cure and with great negative impact on patients' quality of life (QoL). The reported prevalence of psoriasis in countries ranges between 0.09% and 11.4%, making psoriasis a serious global problem with at least 100 million individuals affected worldwide. The most common type of psoriasis is psoriasis vulgaris which is characterized by scaly, red skin, mainly around the elbows, knees and scalp. Psoriasis is characterized by accelerated growth of epidermis cells (keratinocyte cells) accompanied by an inflammation.

According to main embodiments of the present invention, a new carrier cream formulation developed by OWC for psoriasis management was incorporated with different concentrations of *Cannabis* oil (THC, CBD or their combination). The efficacy of the Test items (THC, CBD, β-caryophyllene or their combination, vehicle cream with or without THC, CBD, β-caryophyllene or their combination) was evaluated in the human skin organ culture model (ex vivo). Human skins were obtained from healthy female (age 48-65) undergone abdominal plastic surgery.

The results showed that the topical cream of the present invention (containing the vehicle cream and cannabis oil extract) treats the main symptoms of psoriasis including significant inhibition of cell proliferation and inhibition of major cytokines that serves as proinflammatory mediators in psoriasis.

The topical formulation of the present invention was able to attenuate inflammation characteristics of the skin in a comparable manner to the positive steroid control group (dexamethasone).

In addition, a profound synergistic effect of the vehicle cream and the cannabis oil extracts with respect to cell proliferation was shown compared to the effect provided by each component when administered separately in a similar concentration.

The present invention is focused on discovering and developing cannabis-based novel therapeutics products and treatments specifically designed for several medical conditions, including inflammatory skin pathologies. It is herein demonstrated that cannabis-based extract and topical formulation disclosed by the present invention are able to attenuate inflammatory characteristics.

The present invention provides cannabis-based formulations and treatments for dermatological conditions, particularly hyperproliferative and/or inflammatory skin disorders, also inflammatory skin diseases, which are a significant part of dermatopathology.

It is further within the scope of the present invention to demonstrate and provide experimental evidence such as clinical trials for the use of cannabis as anti-proliferative and/or anti-inflammatory skin conditions and diseases such as a psoriasis treatment. According to some aspects, the present invention shows that the inhibitory effect of cannabinoids on proliferation and its anti-inflammatory effect, make cannabinoids a good psoriasis treatment, albeit with health concerns in connection with smoking and overuse.

According to one embodiment, the present invention provides a pharmaceutical topical composition comprising:
 a. a carrier formulation, comprising at least two of:
  i. Glycerin;
  ii. Niacinamide;
  iii. Salicylic Acid; and
  iv. β-Caryophyllene; and
 b. *Cannabis* oil comprising cannabidiol (CBD) or a derivative thereof and Tetrahydrocannabinol (THC) or a derivative thereof in an about 1:1 ratio According to a core aspect of the present invention, the composition provides a synergistic effect with respect to treatment of, or inhibition of hyperproliferative and/or inflammatory skin conditions as compared to the effect provided by said carrier formulation or said *Cannabis* oil administered separately in similar concentrations.

According to another embodiment of the present invention, the pharmaceutical topical composition as defined above, further comprises at least one ingredient selected from the group consisting of: Glyceryl Stearate & PEG-100 Stearate, Cetyl Alcohol, Allantoin, Butyrospermum Parkii, Petrolatum, Steareth-21, Tocopheryl Acetate, Lavandula Angustifolia oil, Xanthan Gum, Dipotassium Glycyrrhizate, Aloe Barbadensis Leaf Juice, Triethanolamine, Bisabolol, Disodium EDTA, vitamin B3, keratolytic agent, anti irritation agent, anti oxidant, terpene, cannabis terpene, anti skin redness agent, antiadherent, binder, coating, disintegrant, flavour, colour, lubricant, glidant, sorbent, preservative, filler, emulsifier, humectant, thickener, skin nourishing agent, skin moistening agent, occlusive agent, emollient agent, calming agent, natural smell agent, suspending agent, soothing agent, pH adjustment agent, complexant, purified water, Shea Butter, Lavender Oil, and any combination thereof.

According to another embodiment of the present invention, the concentration of said CBD or said derivative thereof and said THC or a derivative thereof is about CBD:THC 3%:3%.

According to another embodiment of the present invention, the composition comprises β-caryophyllene in about 0.5% concentration.

The term "about" refers hereinafter to ±25% of the defined amount or measure or value.

The term "hyperproliferative and/or inflammatory skin conditions" or "inflammatory skin disorders" or "inflammatory skin diseases" or "inflammatory skin conditions" within the scope of the current invention refers to a group of diseases that result in inflammation and/or hyperproliferation of the skin. These diseases may be characterized by itchiness, red skin, and a rash. They can be classified according to the following pattern characteristics:

Bullous.
Interface.
Nodular & diffuse.
Spongiotic.
Vasculitis.
Perivascular.
Panniculitis.
Psoriasiform.

Characteristics of inflammatory skin disease are exemplified in the following table:

| Pattern | Histologic feature | Subclassifications | Example of diseases/disorders |
|---|---|---|---|
| Bullous | large "empty spaces" | subcorneal suprabasillar subepidermal | pemphigus foliaceus pemphigus vulgaris dermatitis herpetiformis |
| Interface | inflammation at DE junction | vacuolar (minimal) lichenoid (band like) | erythema multiforme, SLE lichen planus |
| Nodular & diffuse | intradermal inflammatory infiltrate- nodular and/or diffuse | neutrophic lymphocytic plasmic eosinophilic histocytic | follicular occlusion triad, ruptured cyst/follicle CTCL, reactive plasma cell neoplasm, syphilis eosinophilic cellulitis, Kimura disease granuloma annulare, sarcoidosis, TB |

-continued

| Pattern | Histologic feature | Subclassifications | Example of diseases/disorders |
|---|---|---|---|
| Spongiotic | small empty spaces between keratinocytes- can see squamous bridges (best seen at high power); +/− quasi-microvacuolar appearance | acute subacute chronic | poison ivy nummular dermatitis atopic dermatitis |
| Vasculitis | inflammation of vessel wall/vessel was destruction | small vessel medium vessel large vessel | leukocytoclastic vasculitis PAN giant cell arteritis |
| Perivascular | inflammation around vessels | neutrophilic lymphocytic mastocytic eosinophilic | cellulitis viral exanthem, Rx reaction mastocytosis insect bite, Rx reaction |
| Panniculitis | inflammation of adipose tissue | septal lobular | erythema nodosum, scleroderma panniculitis erythema induratum, infection |
| Psoriasiform | epidermal thickening and long rete ridges | regular irregular | psoriasis lichen simplex chronicus |

It is noted that:
DE junction=dermal-epidermal junction.
The "empty space" in bullous disease in situ is filled with fluid.

According to a further embodiment, examples of inflammatory skin disorders within the scope of the current invention include:

Non-specific patterns such as Psoriasiform pattern;

Specific diseases such as Seborrheic dermatitis, Lupus erythematosus, Discoid lupus erythematosus, Dermatomyositis, Lichen planus, Lichen sclerosus, Psoriasis, Lichen striatus, Lichen aureus, Granuloma faciale, Atopic dermatitis, Sweet syndrome, Granuloma inguinale, Pyoderma gangrenosum, Necrobiotic xanthogranuloma;

Differential Diagnosis (DDx) for pattern, for example Spongiotic dermatitides, Psoriasiform dermatitides (e.g. Regular psoriasiform dermatitis, Irregular psoriasiform dermatitis), Interface dermatitides (e.g. Vacuolar interface dermatitides, Lichenoid interface dermatitides), Bullous disease (e.g. Subcorneal bullous disorders, Suprabasilar bullous disorders, Subepidermal bullous disorders), Dermatitides with perivascular inflammation (Lymphocytes, Neutrophils, Eosinophils, Mast cells), Vasculitis, Nodular and diffuse dermatitides (e.g. Neutrophils, Lymphocytes, Plasma cells, Eosinophils, Histiocytes such as Granulomatous, Sarcoidal, Tuberculoid, Foreign body-type granulomas, Palisaded granumolas).

The term "psoriasis" refers hereinafter to a common, chronic, relapsing, immune-mediated skin disease characterized by red, scaly patches, papules, and plaques, which usually itch. The skin lesions seen in psoriasis may vary in severity from minor localized patches to complete body coverage. More specifically the term relates to five main types of psoriasis: plaque, guttate, inverse, pustular, and erythrodermic. Plaque psoriasis, the most common form, typically manifests as red and white scaly patches on the top layer of the skin. Skin cells rapidly accumulate at these plaque sites and create a silvery-white appearance. Plaques frequently occur on the skin of the elbows and knees, but can affect any area, including the scalp, palms of hands, and soles of feet, and genitals. In contrast to eczema, psoriasis is more likely to be found on the outer side of the joint. Fingernails and toenails are frequently affected (psoriatic nail dystrophy) and can be seen as an isolated sign. Inflammation of the joints, known as psoriatic arthritis, affects up to 30% of individuals with psoriasis.

The term "cannabidiol (CBD)" refers hereinafter to one of at least 85 active cannabinoids identified in cannabis. Cannabidiol is a major phytocannabinoid, accounting for up to 40% of the plant's extract. Cannabidiol (CBD) has little activity at cannabinoid type 1 receptors (CB1) but greater activity at the cannabinoid type 2 receptors (CB2). CBD is a non-competitive CB1/CB2 receptor antagonist. CBD may potentiate THC's effects by increasing CB1 receptor density or through another CB1-related mechanism. It is also an inverse agonist of CB2 receptors. CBD possesses anti-inflammatory, antiproliferative, pro-apoptotic effects and inhibits cancer cell migration, adhesion and invasion.

The term "Tetrahydrocannabinol (THC)" refers hereinafter to the principal psychoactive constituent (or cannabinoid) of the cannabis plant. THC has a partial agonist activity at the cannabinoid receptor CB1, and the CB2 receptor.

The term "β-caryophyllene" refers hereinafter to a terpenoid constituent of the cannabis plant. β-caryophyllene has a partial agonist activity at the cannabinoid receptor CB2 receptor.

The term "THC rich cannabis strain" refers hereinafter to a cannabis strain having 20% or more THC.

The term "CBD rich cannabis strain" refers hereinafter to a cannabis strain having 1% or more CBD.

The term "cannabinoid receptor" refers hereinafter to a class of cell membrane receptors under the G protein-coupled receptor superfamily. There are currently two known subtypes of cannabinoid receptors, termed CB1 and CB2. The CB1 receptor is expressed mainly in the brain, but also in the lungs, liver and kidneys. The CB2 receptor is expressed mainly in the immune system and in hematopoietic cells.

The term "Cannabinoid receptor type 1 (CB1)" refers hereinafter to a G protein-coupled cannabinoid receptor located primarily in the central and peripheral nervous system. It is activated by the endocannabinoid neurotransmitters anandamide and 2-arachidonoyl glyceride (2-AG); by plant cannabinoids, such as the compound THC, an active ingredient of the psychoactive drug cannabis; and by synthetic analogues of THC.

The term "Cannabinoid receptor type 2 (CB2)" refers hereinafter to a G protein-coupled receptor from the cannabinoid receptor family that in humans is encoded by the CNR2 gene. It is closely related to the cannabinoid receptor type 1, which is largely responsible for the efficacy of endocannabinoid-mediated presynaptic-inhibition, the psychoactive properties of Tetrahydrocannabinol, the active agent in marijuana, and other phytocannabinoids (natural cannabinoids). The principal endogenous ligand for the CB2 receptor is 2-arachidonoylglycerol (2-AG).

The term "nonpsychoactive" refers hereinafter not affecting the mind or mental processes.

The term "cannabinoid" refers hereinafter to a class of diverse chemical compounds that act on cannabinoid receptors on cells that repress neurotransmitter release in the brain. These receptor proteins include the endocannabinoids (produced naturally in the body by humans and animals), the phytocannabinoids (found in cannabis and some other plants), and synthetic cannabinoids.

The term "sustained release dosage form" refers hereinafter to the release of a drug at a predetermined rate in order to maintain a constant drug concentration for a specific period of time with minimum side effects. This can be achieved through a variety of formulations, including liposomes and drug-polymer conjugates. Sustained release's definition is more akin to a "controlled release" rather than "sustained".

The term "Psoriasis Area and Severity Index (PASI)" refers hereinafter to most widely used tool for the measurement of severity of psoriasis. PASI combines the assessment of the severity of lesions and the area affected into a single score in the range 0 (no disease) to 72 (maximal disease). The body is divided into four sections (head (H) (10% of a person's skin); arms (A) (20%); trunk (T) (30%); legs (L) (40%)). Each of these areas is scored by itself, and then the four scores are combined into the final PASI. For each section, the percent of area of skin involved, is estimated and then transformed into a grade from 0 to 6:

0% of involved area, grade: 0
<10% of involved area, grade: 1
10-29% of involved area, grade: 2
30-49% of involved area, grade: 3
50-69% of involved area, grade: 4
70-89% of involved area, grade: 5
90-100% of involved area, grade: 6

Within each area, the severity is estimated by three clinical signs: erythema (redness), induration (thickness) and desquamation (scaling). Severity parameters are measured on a scale of 0 to 4, from none to maximum. The sum of all three severity parameters is then calculated for each section of skin, multiplied by the area score for that area and multiplied by weight of respective section (0.1 for head, 0.2 for arms, 0.3 for body and 0.4 for legs).

The term "Test item" or "Test items" refers hereinafter to an ingredient, combination of ingredients or formulation which is evaluated for its effect on improving one or more dermatological condition symptoms ex-vivo, in vitro and/or in-vivo.

As used herein, the term "carrier formulation" or "base formulation" or "vehicle formulation" or "placebo" refers to a control formulation containing inactive ingredients as demonstrated in Table 1 (without β-caryophyllene and cannabis oil) and/or Table 3 (without β-caryophyllene). In some embodiments, where indicated, the base formulation is supplemented with 0.5% β-caryophyllene. It is noted that the base formulation was used as a control in the experiments described by the present disclosure. Furthermore, the base formulation was used to produce combinations with preselected ingredients in order to test synergistic effects of the combination as compared to each of the ingredients alone or their partial combinations. Examples of preselected combinations include the base formulation with at least one of β-caryophyllene, CBD extract, THC extract, different ratios of CBD and THC. The combinations have been prepared "on site", which means that the preparation was performed by mixing (e.g. constant stirring) the placebo/base formulation with the indicated amount of ingredient or extract.

The term "topical formulation" refers hereinafter to the final formulation containing the base formulation as demonstrated in Table 2 in combination with β-caryophyllene and a combination of both CBD or THC. In some embodiments, the CBD:THC ratio in the topical formulation is about 1:1. In preferred embodiments, the topical formulation is a "ready to use" formulation or a stock formulation containing the ingredients required to perform the desirable effect. An exemplified topical cream formulation is demonstrated in Table 8 of this disclosure. In some embodiments, the final CBD:THC concentration in the topical formulation is about 3%:3%. According to further embodiments, the topical formulation additionally comprises 0.5% β-caryophyllene.

The term "Epidermal turnover time" or "Epidermal turnover rate" refers hereinafter to proliferation rate of the epidermis.

The present invention provides a pharmaceutical composition comprising therapeutically effective amount of, or an extract consisting essentially therapeutically effective amount of at least one cannabinoid selected from the group consisting of: cannabidiol (CBD) or a derivative thereof, Tetrahydrocannabinol (THC) or a derivative thereof, and any combination thereof, for use in the treatment of hyperproliferative and/or inflammatory skin disorders and conditions such as psoriasis.

According to one aspect, the cannabidiol (CBD) or a derivative thereof and Tetrahydrocannabinol (THC) or a derivative thereof of the composition of the present invention are acting as modulators of the endocannabinoid system activity. According to other aspects theses cannabinoids may cause alteration of the inflammatory and inhibit keratinocyte proliferation.

According to a further embodiment, the Psoriasis Area and Severity Index (PASI) is used to assess the effect of the cannabinoid composition of the present invention on relieving psoriasis symptoms.

According to one embodiment, the present invention provides a pharmaceutical composition comprising a therapeutically effective amount of at least one cannabinoid selected from the group consisting of: cannabidiol (CBD) or a derivative thereof, Tetrahydrocannabinol (THC) or a derivative thereof, and a combination thereof, useful for treatment or prevention of psoriasis.

It is further within the scope to provide the pharmaceutical composition as defined in any of the above, wherein the concentration of the CBD or the derivative thereof is in the range of about 2% to about 40%.

It is further within the scope to provide the pharmaceutical composition as defined in any of the above, wherein the concentration of the THC or the derivative thereof is in the range of about 2% to about 40%.

It is further within the scope to provide the pharmaceutical composition as defined in any of the above, wherein the composition comprises cannabis oil.

It is further within the scope to provide the pharmaceutical composition as defined in any of the above, wherein the composition comprises about 10% cannabis oil.

It is further within the scope to provide the pharmaceutical composition as defined in any of the above, wherein the cannabis oil comprises about 30% THC and about 30% CBD, resulting in 3% THC and 3% CBD in the final formulation.

It is further within the scope to provide the pharmaceutical composition as defined in any of the above, wherein the composition is administered in a route selected from the group consisting of: intranasal, transdermal, intravenous, oral, topical and any combination thereof.

It is further within the scope to provide the pharmaceutical composition as defined in any of the above, wherein the composition is formulated in a form selected from the group consisting of cream, ointment, lotion, foam, film, transdermal patch and any combination thereof.

It is further within the scope to provide the pharmaceutical composition as defined in any of the above, wherein the composition is administered in combination with an additional psoriasis therapeutic agent; the additional psoriasis therapeutic agent is selected from the group consisting of methotrexate, ciclosporin, hydroxycarbamide, fumarates, retinoids, efalizumab, vitamin D or derivatives thereof, alefacept and any combination thereof.

It is further within the scope to provide the pharmaceutical composition as defined in any of the above, wherein the composition combined with at least one psoriasis therapeutic agent provides a synergistic effect with respect to treating or preventing psoriasis relative to the effect provided by the psoriasis therapeutic agent administered separately.

It is further within the scope to provide the pharmaceutical composition as defined in any of the above, wherein the composition is formulated to prevent or treat psoriasis in a condition in which the same is induced; the condition is selected from the group consisting of: chronic infection, stress, climate or season change, skin dryness, excessive alcohol consumption, cigarette smoking, and obesity, withdrawal of a systemic corticosteroid, oxidative stress, use of include beta blockers, lithium, antimalarial medications, non-steroidal anti-inflammatory drugs, terbinafine, calcium channel blockers, captopril, glyburide, granulocyte colony-stimulating factor, interleukins, interferons, lipid-lowering drugs or TNF inhibitors, and any combination thereof.

It is further within the scope to provide the pharmaceutical composition as defined in any of the above, wherein the CBD or the derivative thereof interacts with at least one receptor selected from the group consisting of Cannabinoid receptor type 1 (CB1), Cannabinoid receptor type 2 (CB2), and any combination thereof.

It is further within the scope to provide the pharmaceutical composition as defined in any of the above, wherein the THC or the derivative thereof interacts with at least one receptor selected from the group consisting of Cannabinoid receptor type 1 (CB1), Cannabinoid receptor type 2 (CB2), and any combination thereof.

It is further within the scope to provide the pharmaceutical composition as defined in any of the above, wherein the composition additionally comprises at least one ingredient selected from the group consisting of cannabis oil, vitamin B3, keratolytic agent, anti irritation agent, anti oxidant, terpenes, cannabis terpenes, anti skin redness agent and any combination thereof.

It is further within the scope to provide the pharmaceutical composition as defined in any of the above, wherein the composition additionally comprises at least one ingredient selected from the group consisting of *Cannabis* Seed Oil, Niacinamide, Salicylic Acid, Allantoin, Tocopheryl Acetate (Vitamin E), β-Caryophyllene and any combination thereof.

It is further within the scope to provide the pharmaceutical composition as defined in any of the above, wherein the composition additionally comprises at least one inactive ingredient or excipient selected from the group consisting of antiadherent, binder, coating, disintegrant, flavour, colour, lubricant, glidant, sorbent, preservative, filler, emulsifier, humectant, thickener, skin nourishing agent, skin moistening agent, occlusive agent, emollient agent, calming agent, natural smell agent, suspending agent, soothing agent, pH adjustment agent, complexant and any combination thereof.

It is further within the scope to provide the pharmaceutical composition as defined in any of the above, wherein the composition additionally comprises at least one inactive ingredient or excipient selected from the group consisting of purified water, Glyceryl Stearate, PEG-100 Stearate, Glycerin, Cetyl Alcohol, Butyrospermum Parkii (Shea Butter), Petrolatum, Steareth-21, Lavandula Angustifolia (Lavender) Oil, Xanthan Gum, Dipotassium Glycyrrhizate, Aloe Barbadensis Leaf Juice, Triethanolamine, Bisabolol, Disodium EDTA and any combination thereof.

It is further within the scope to provide the pharmaceutical composition as defined in any of the above, wherein the composition is in a sustained release dosage form.

It is further within the scope to provide the pharmaceutical composition as defined in any of the above, wherein the sustained release dosage form is selected from the group consisting of liposomes, drug polymer conjugates, microencapsulation, controlled-release tablet coating, and any combination thereof.

It is further within the scope to provide the pharmaceutical composition as defined in any of the above, wherein the composition is in a rapid release dosage form.

It is further within the scope to provide the pharmaceutical composition as defined in any of the above, wherein the composition is not significantly psychoactive.

It is further within the scope to provide the pharmaceutical composition as defined in any of the above, wherein the composition is administered once, twice, three or four times through the day.

It is further within the scope to provide the pharmaceutical composition as defined in any of the above, wherein the CBD, THC or a combination thereof is extracted from at least one cannabis plant.

It is further within the scope to provide the pharmaceutical composition as defined in any of the above, wherein the cannabis plant is a CBD rich strain.

It is further within the scope to provide the pharmaceutical composition as defined in any of the above, wherein the cannabis plant is a THC rich strain.

It is further within the scope to provide the pharmaceutical composition as defined in any of the above, wherein the CBD or derivative thereof is produced by a synthetic route.

It is further within the scope to provide the pharmaceutical composition as defined in any of the above, wherein the THC or derivative thereof is produced by a synthetic route.

It is further within the scope to provide the pharmaceutical composition as defined in any of the above, wherein the composition is dissolved in a lipophilic solvent or suspension carrier.

It is further within the scope to provide the pharmaceutical composition as defined in any of the above, wherein the lipophilic solvent or suspension carrier are selected from a group consisting of medium-chain triglyceride, short-chain triglyceride, medium-chain partial glyceride, polyoxyethylated fatty alcohol, polyoxyethylated fatty acid, polyoxyethylated fatty acid triglyceride or partial glyceride, ester of fatty acids with low molecular weight alcohols, a partial ester of sorbitan with fatty acids, a polyoxyethylated partial ester of sorbitan with fatty acids, a partial ester of sugars or oligomeric sugars with fatty acids, a polyethylene glycol, lecithin, vegetable oil, and any combination thereof.

It is further within the scope to provide the pharmaceutical composition as defined in any of the above, wherein the composition provides a synergistic effect with respect to treating or preventing psoriasis as compared to the effect provided by the THC or a derivative thereof or by the CBD or a derivative thereof administered separately in a similar concentration.

It is further within the scope to provide the pharmaceutical composition as defined in any of the above, wherein the composition provides an improvement in psoriasis symptoms of a patient as measured by Psoriasis Area and Severity Index (PASI), compared to an established baseline or placebo or control.

It is further within the scope to provide the pharmaceutical composition as defined in any of the above, wherein the improvement in psoriasis symptoms of the patient is measured by a decrease in the patient's score of at least one point or level of the PASI, as compared to an established baseline or to a placebo or control.

It is further within the scope to provide the pharmaceutical composition as defined in any of the above, wherein the symptoms are selected from the group consisting of erythema, redness, induration, thickness, desquamation, scaling, red patches of skin covered with silvery scales, small scaling spots, dry skin, cracked skin that may bleed, itching, burning, soreness, thickened, pitted or ridged nails, swollen and stiff joints, and any combination thereof.

It is further within the scope to provide the pharmaceutical composition as defined in any of the above, wherein the composition is formulated for administration of a dosage of up to about 1500 mg, preferably a dosage in the range of about 100 mg to about 1500 mg from the final formulation, more preferably a dosage of up to about 30 mg of an active ingredient selected from the group consisting of CBD, THC, β-Caryophyllene and any combination thereof, per day.

It is a further embodiment to provide a method of treating or preventing psoriasis in a subject comprising steps of: (a) providing a composition comprising Tetrahydrocannabinol (THC) or a derivative thereof, or Cannabidiol (CBD) or a derivative thereof, or a combination thereof; and (b) administering the composition to the patient at a therapeutically effective dosage for treating or preventing psoriasis of the subject.

It is further within the scope to provide the method as defined above, additionally comprising steps of providing the CBD or the derivative thereof is in a concentration in the range of about 2% to about 40%.

It is further within the scope to provide the method as defined in any of the above, additionally comprising steps of providing the THC or the derivative thereof is in a concentration in the range of about 2% to about 40%.

It is further within the scope to provide the method as defined in any of the above, additionally comprising steps of providing the composition comprising cannabis oil.

It is further within the scope to provide the method as defined in any of the above, additionally comprising steps of providing the composition comprising about 10% cannabis oil.

It is further within the scope to provide the method as defined in any of the above, additionally comprising steps of providing the cannabis oil comprising about 30% THC and about 30% CBD, 5% β-caryophyllene resulting in 3% THC and 3% CBD and 0.5% β-caryophyllene in the final formulation.

It is further within the scope to provide the method as defined in any of the above, additionally comprising steps of administering the composition in a route selected from a group consisting of: intranasal, transdermal, intravenous, oral, topical, and any combination thereof.

It is further within the scope to provide the method as defined in any of the above, additionally comprising steps of administering the composition topically in a formulation selected from the group of preparations consisting of cream, ointment lotion, foam, film, transdermal patch and any combination thereof.

It is further within the scope to provide the method as defined in any of the above, additionally comprising steps of administering the composition over a time period of about 1 day to about 6 months.

It is further within the scope to provide the method as defined in any of the above, additionally comprising steps of administering the composition in a dosage of CBD of up to 100 mg per day, preferably in the range of about 10 mg to about 100 mg per day, more preferably in a dosage of up to about 30 mg per day.

It is further within the scope to provide the method as defined in any of the above, additionally comprising steps of administering the composition in a dosage of THC of up to 100 mg per day, preferably in the range of about 10 mg to about 100 mg per day, more preferably in a dosage of up to about 30 mg per day.

It is further within the scope to provide the method as defined in any of the above, additionally comprising steps of administering the composition in a dosage of β-Caryophyllene of up to 100 mg per day, preferably in the range of about 3 mg to about 10 mg per day, more preferably in a dosage of up to about 5 mg per day.

It is further within the scope to provide the method as defined in any of the above, additionally comprising steps of administering the composition once, twice, three or four times through the day.

It is further within the scope to provide the method as defined in any of the above, additionally comprising steps of administering the composition with an additional psoriasis therapeutic agent; the additional psoriasis therapeutic agent is selected from a group consisting of methotrexate, ciclosporin, hydroxycarbamide, fumarates, retinoids, efalizumab and alefacept, vitamin D or derivatives thereof and any combination thereof.

It is further within the scope to provide the method as defined in any of the above, additionally comprising steps of administering the composition with an additional psoriasis therapeutic agent to provide a synergistic effect with respect to treating or preventing psoriasis relative to the effect provided by the psoriasis therapeutic agent administered separately.

It is further within the scope to provide the method as defined in any of the above, additionally comprising steps of preventing or treating psoriasis in a condition in which the same is induced; the condition is selected from the group consisting of: chronic infection, stress, climate or season change, skin dryness, excessive alcohol consumption, cigarette smoking, and obesity, withdrawal of a systemic corticosteroid, oxidative stress, use of include beta blockers, lithium, antimalarial medications, non-steroidal anti-inflammatory drugs, terbinafine, calcium channel blockers, captopril, glyburide, granulocyte colony-stimulating factor, interleukins, interferons, lipid-lowering drugs or TNF inhibitors, and any combination thereof.

It is further within the scope to provide the method as defined in any of the above, additionally comprising steps of formulating the composition with at least one ingredient selected from the group consisting of cannabis oil, vitamin B3, keratolytic agent, anti irritation agent, anti oxidant, terpenes, cannabis terpenes, anti skin redness agent and any combination thereof.

It is further within the scope to provide the method as defined in any of the above, additionally comprising steps of formulating the composition with at least one ingredient selected from the group consisting of *Cannabis* Seed Oil, Niacinamide, Salicylic Acid, Allantoin, Tocopheryl Acetate (Vitamin E), β-Caryophyllene and any combination thereof.

It is further within the scope to provide the method as defined in any of the above, additionally comprising steps of formulating the composition with at least one inactive ingredient or excipient selected from the group consisting of antiadherent, binder, coating, disintegrant, flavour, colour, lubricant, glidant, sorbent, preservative, filler, emulsifier, humectant, thickener, skin nourishing agent, skin moistening agent, occlusive agent, emollient agent, calming agent, natural smell agent, suspending agent, soothing agent, pH adjustment agent, complexant and any combination thereof.

It is further within the scope to provide the method as defined in any of the above, additionally comprising steps of formulating the composition with at least one inactive ingredient or excipient selected from the group consisting of purified water, Glyceryl Stearate, PEG-100 Stearate, Glycerin, Cetyl Alcohol, Butyrospermum Parkii (Shea Butter), Petrolatum, Steareth-21, Lavandula Angustifolia (Lavender) Oil, Xanthan Gum, Dipotassium Glycyrrhizate, Aloe Barbadensis Leaf Juice, Triethanolamine, Bisabolol, Disodium EDTA and any combination thereof.

It is further within the scope to provide the method as defined in any of the above, additionally comprising steps of formulating the composition in a sustained release dosage form.

It is further within the scope to provide the method as defined in any of the above, additionally comprising steps of formulating the composition in a sustained release dosage form selected from the group consisting of liposomes, drug polymer conjugates, microencapsulation, controlled-release tablet coating, and any combination thereof.

It is further within the scope to provide the method as defined in any of the above, additionally comprising steps of formulating the composition in a rapid release dosage form.

It is further within the scope to provide the method as defined in any of the above, wherein the administration does not cause a significant psychoactive effect.

It is further within the scope to provide the method as defined in any of the above, additionally comprising steps of administering the CBD with Tetrahydrocannabinol (THC) in a concentration which is equal or less than 3% of each cannabinoid.

It is further within the scope to provide the method as defined in any of the above, additionally comprising steps of providing a synergistic effect with respect to treating or preventing psoriasis of the subject as compared to the effect provided by a combination of THC or a derivative thereof and CBD or a derivative thereof together with a formulation administered separately in a similar concentration.

It is further within the scope to provide the method as defined in any of the above, additionally comprising steps of providing an improvement in psoriasis symptoms of the subject as measured by Psoriasis Area and Severity Index (PASI) compared to an established baseline or placebo or control.

It is further within the scope to provide the method as defined in any of the above, additionally comprising steps of providing an improvement in psoriasis symptoms of the subject as measured by a decrease in the patient's score of at least one point or level of the PASI, as compared to an established baseline or to a placebo or control.

It is further within the scope to provide the method as defined in any of the above, additionally comprising steps of selecting the symptoms from the group consisting of erythema, redness, induration, thickness, desquamation, scaling, red patches of skin covered with silvery scales, small scaling spots, dry skin, cracked skin that may bleed, itching, burning, soreness, thickened, pitted or ridged nails, swollen and stiff joints, and any combination thereof.

It is a further embodiment of the present invention to provide a use of a composition comprising a therapeutically effective amount of at least one cannabinoid selected from the group consisting of: cannabidiol (CBD) or a derivative thereof, Tetrahydrocannabinol (THC) or a derivative thereof, and a combination thereof, in the manufacture of a medicament for treating or preventing psoriasis.

It is further within the scope to provide the use as defined above, additionally comprising steps of providing the composition with CBD in a concentration in the range of about 2% to about 40%.

It is further within the scope to provide the use as defined in any of the above, additionally comprising steps of providing the composition with THC concentration in the range of about 2% to about 40%.

It is further within the scope to provide the use as defined in any of the above additionally comprising steps of providing the composition comprising cannabis oil or ethanol extract of cannabis.

It is further within the scope to provide the use as defined in any of the above, additionally comprising steps of providing the composition comprising about 10% cannabis oil.

It is further within the scope to provide the use as defined in any of the above, additionally comprising steps of providing the cannabis oil comprising about 30% THC and about 30% CBD, resulting in 3% THC and 3% CBD in the final formulation.

It is further within the scope to provide the use as defined in any of the above, additionally comprising steps of administering the composition in a route selected from a group consisting of: intranasal, transdermal, intravenous, oral, topical, and any combination thereof.

It is further within the scope to provide the use as defined in any of the above, additionally comprising steps of administering the composition topically in a formulation selected from a group of preparations consisting of cream, ointment lotion, foam, transdermal patch, film and any combination thereof.

It is further within the scope to provide the use as defined in any of the above, additionally comprising steps of administering the composition over a time period of about 1 day to about 6 months.

It is further within the scope to provide the use as defined in any of the above, additionally comprising steps of administering the composition in a dosage of CBD of up to 100 mg per day, preferably in the range of about 10 mg to about 100 mg per day, more preferably in a dosage of up to about 30 mg per day.

It is further within the scope to provide the use as defined in any of the above, additionally comprising steps of administering the composition in a dosage of THC of up to 100 mg per day, preferably in the range of about 10 mg to about 100 mg per day, more preferably in a dosage of up to about 30 mg per day.

It is further within the scope to provide the use as defined in any of the above, additionally comprising steps of administering the composition in a dosage of β-Caryophyllene of up to 100 mg per day, preferably in the range of about 3 mg to about 10 mg per day, more preferably in a dosage of up to about 5 mg per day.

It is further within the scope to provide the use as defined in any of the above, additionally comprising steps of administering the composition once, twice, three or four times through the day.

It is further within the scope to provide the use as defined in any of the above, additionally comprising steps of administering the composition with an additional psoriasis therapeutic agent; the additional psoriasis therapeutic agent is selected from a group consisting of methotrexate, ciclosporin, hydroxycarbamide, fumarates, retinoids, efalizumab, vitamin D and alefacept and any combination thereof.

It is further within the scope to provide the use as defined in any of the above, additionally comprising a step of treating or preventing psoriasis in conditions in which the same is induced; the conditions are selected from a group consisting of: chronic infection, stress, climate or season change, skin dryness, excessive alcohol consumption, cigarette smoking, and obesity, withdrawal of a systemic corticosteroid, oxidative stress, use of include beta blockers, lithium, antimalarial medications, non-steroidal anti-inflammatory drugs, terbinafine, calcium channel blockers, captopril, glyburide, granulocyte colony-stimulating factor, interleukins, interferons, lipid-lowering drugs or TNF inhibitors, and any combination thereof.

It is further within the scope to provide the use as defined in any of the above, additionally comprising steps of formulating the composition in a sustained release dosage form; the sustained release dosage form is selected from a group consisting of liposomes, drug polymer conjugates, microencapsulation, controlled-release tablet coating, and any combination thereof.

It is further within the scope to provide the use as defined in any of the above, wherein the administration does not cause a significant psychoactive effect.

It is further within the scope to provide the use as defined in any of the above, additionally comprising steps of administering the CBD with Tetrahydrocannabinol (THC) in a concentration which is equal or less than 3% from each cannabinoid.

It is further within the scope to provide the use as defined in any of the above, additionally comprising steps of providing a synergistic effect with respect to treating or preventing psoriasis of the subject as compared to the effect provided by the THC or a derivative thereof or by the CBD or a derivative thereof administered separately in a similar concentration.

It is further within the scope to provide the use as defined in any of the above, additionally comprising steps of providing an improvement in psoriasis symptoms of the subject as measured by Psoriasis Area and Severity Index (PASI), compared to an established baseline or placebo or control.

It is further within the scope to provide the use as defined in any of the above, additionally comprising steps of providing an improvement in psoriasis symptoms of the subject as measured by a decrease in the patient's score of at least one point or level of the PASI, as compared to an established baseline or to a placebo or control.

It is further within the scope to provide the use as defined in any of the above, additionally comprising steps of selecting the symptoms from the group consisting of erythema, redness, induration, thickness, desquamation, scaling, red patches of skin covered with silvery scales, small scaling spots, dry skin, cracked skin that may bleed, itching, burning, soreness, thickened, pitted or ridged nails, swollen and stiff joints, and any combination thereof.

In order to understand the invention and to see how it may be implemented in practice, a plurality of preferred embodiments will now be described, by way of non-limiting example only, with reference to the following examples.

Example 1

A Topical Formulation Containing *Cannabis* for Treating Psoriasis and Other Inflammatory Dermatological Conditions Reference is now made to an exemplified topical formulation containing *Cannabis* for treating inflammatory skin pathologies and conditions such as psoriasis, as an embodiment of the present invention.

The topical cream formulation has the following advantageous characteristics: it contains *Cannabis* oil and β-Caryophyllene as active ingredients, it has an acidic pH, it contains high concentration of Salicylic Acid (reported by the FDA to be effective against psoriasis), it is enriched in anti irritation and anti inflammation agents effective against symptoms of dermatological disorders (i.e. inflammation and redness of the skin) and it is enriched in skin moistening and nourishing agents. The cannabis oil ingredient within the cream comprises a final concentration of about 3% THC and about 3% CBD. Table 1 presents ingredients of a topical formulation containing cannabis oil, as an embodiment of the present invention.

TABLE 1

A topical formulation of the present invention containing cannabis oil

| Ingredients: | Function: |
| --- | --- |
| Purified Water | Filler |
| Glyceryl Stearate & PEG 100 Stearate | Emulsifier (acid stable) |
| Cannabis oil | Cannabis oil |
| Glycerin | Humectant |
| Niacinamide | Vitamin B3 |
| Cetyl Alcohol | Thickener |
| Salicylic Acid | Keratolytic agent |
| Allantoin | Anti irritation |
| *Butyrospermum Parkii* (Shea Butter) | Skin nourishing and healing |
| Petrolatum | Occlusive & emollient agent |
| Steareth 21 | Emulsifier |
| Tocopheryl Acetate (Vitamin E) | Anti oxidant |
| *Lavandula Angustifolia* (Lavender) Oil | Calming & natural smell |
| β-Caryophyllene 0.5% | A terpene in cannabis |
| Xanthan Gum | Suspending agent |
| Dipotassium Glycyrrhizate | Soothing & anti redness anti psoriasis effect |
| Aloe *Barbadensis* Leaf Juice | Calming & soothing |
| Triethanolamine | pH adjustment |
| Bisabolol | Soothing & calming |
| Disodium EDTA. | Complexant |

Example 2

Anti-Inflammatory Evaluation of *Cannabis*-Based Extracts and Topical Formulations in Human Skin Organ Culture Abbreviations DMEM Dulbecco Minimal Essential Medium
MTT (3-(4,5-Dimethylthiazol-2-yl)-2,5-Diphenyltetrazolium Bromide)
min Minute(s)
hr Hour(s)
ELISA Enzyme-Linked Immunosorbent Assay
PBS Phosphate Saline Buffer
RT Room Temperature TBD To Be Determined
IL Interleukin
SEM Standard Error of Mean
n Population Size
RPM Revolutions per minute
LPS Lipopolysaccharide
EGF Epidermal Growth Factor
SOP Standard Operating Procedure
SD Standard Deviation Objectives The objective of the study was to evaluate the anti-inflammatory activity of the Test items. In this study, the efficacy of the Test items was evaluated in a human skin organ culture model (ex-vivo). The skin explants were stimulated with LPS/EGF mixture or with TNFα to induce inflammation condition or to induce hyperproliferation, and treated without or with several concentrations of the Test items. Cytokine levels and the epidermis turnover rate were monitored under the various treatments. Additionally, the study included negative, vehicle and positive controls.

Materials and Methods

Reference is now made to a materials list presented in Table 2 below.

TABLE 2

Material List

| No./Name | Manufacturer/Supplier | Cat No./Lot No. | Physical State/Storage Conditions | Expiry Date | Name in the report |
|---|---|---|---|---|---|
| Test Items | | | | | |
| 1. Test item 1 | Bazelet OWC | OWC 1.1 THC 16217 | Liquid RT | n/a | Test item 1 |
| 2. Test item 2 | Bazelet OWC | OWC 1.2 CBD 26217 | Liquid RT | n/a | Test item 2 |
| 3. Test item 3 | Bazelet OWC | OWC 1.3 THC-CBD 36217 | Liquid RT | n/a | Test item 3 |
| 4. Test item, formulated | OWC OWC | PSO-1-2015 N/A | TBD TBD | n/a | Test item, formulated |
| 5. Psoriasis cream* placebo | OWC OWC | OWC-PSO-1-2015 placebo (2) | Formulation RT | n/a | Vehicle formulation |
| 6. Test item 4 | Bazelet OWC | OWC 1:1 THC/CBD 17191 | Liquid RT | n/a | Test item 4 (oil) |
| 7. Test item 5 | Bazelet OWC | OWC 2 THC 27191 | Liquid RT | n/a | Test item 5 (oil) |
| 8. Test item 6 | Bazelet OWC | OWC 3 CBD 37191 | Liquid RT | n/a | Test item 6 (oil) |
| Skin culture medium | | | | | |
| 9. DMEM | Biological Industries Biological Industries | 01-052-1A 1643856 | Liquid 2-8° C. | 10/17 | DMEM |
| 10. Penicillin-streptomycin solution | Biological Industries Biological Industries | 03-033-1B 1628553 | Frozen (−25)-(−15)° C. | 1/18 | Pen Strep |
| Other chemicals | | | | | |
| 11. PBS | Biological Industries Biological Industries | 02-023-1A 1545510 | Liquid RT | 11/17 | PBS |
| 12. MTT | Sigma Aldrich Sigma Aldrich | M56555MG MKBX6776V | Powder (−25)-(−15)° C. | 5/16 | MTT |
| 13. β-caryophyllene | Sigma Aldrich Sigma Aldrich | 22075-5MF BLB90948V | Liquid 2-8° C. | 1/18 | β-caryophyllene |
| 14. Dexamethasone | Sigma Aldrich Sigma Aldrich | D175614 BCBP8678V | Powder 2-8° C. | 2/20 | Dexamethasone |
| Marker quantification | | | | | |
| 15. ELISA Max Deluxe Set Human IL-8 | BioLegend Enco | 431505 B177581 | N/A 2-8° C. | 1/18 | IL-8 ELISA kit |

TABLE 2-continued

| | | | | | |
|---|---|---|---|---|---|
| 16. ELISA Max Deluxe Set Human IL-6 | BioLegend Enco | 430506 B223180 | N/A 2-8° C. | 1/18 | IL-6 ELISA kit |
| 17. ELISA Max Deluxe Set Human IL-1α | BioLegend Enco | 434906 B214084 | BioLegend Enco | 1/18 | IL-1α ELISA kit |
| 18. IL-33 ELISA kit | Peprotech Peprotech | 900-K398 1208398 | N/A (−25)-(−15)° C. | 12/18 | IL-33 ELISA kit |
| 19. IL-17 ELISA kit | BioLegend Enco | 433916 B207362 | N/A 2-8° C. | 12/17 | IL-17 ELISA kit |
| 20. IL-12 ELISA kit | BioLegend Enco | 430706 B1S2486 | N/A 2-8° C. | 12/17 | IL-12 ELISA kit |
| 21. BrdU ELISA Kit | Abcam Zotal | Ab126556 9R302878-1 | N/A 2-8° C. | N/A | BrdU |

*For product data sheet see Table 3

Formulations

All formulations were prepared under sterile conditions.

Skin Culture Medium:

DMEM will be supplemented with 100 U/ml penicillin and 100 μg/ml streptomycin, filtered.

MTT (3-(4,5-Dimethylthiazol-2-yl)-2,5-Diphenyltetrazolium Bromide)

MTT stock (10×): MTT powder was dissolved in PBS to prepare a 5 mg/ml stock solution. The stock was filtered through 0.2 micron filter, aliquoted and stored at −20° C. At the day of assay, the stock was diluted 1:10 in PBS.

Test Item:

Unless written otherwise, the Test items and vehicle formulation were received sterile and ready to use in their final concentration. All materials were kept in reduced light and humidity conditions at RT.

The Test item "on site" preparation was performed by constant stirring of the placebo formulation with the indicated amount of extracts for 10 min, at RT.

Disposal of Materials

The disposal of samples will be carried out by the test facility. Place the samples into a bio hazard bag and dispose it into the central bio hazard container.

General Equipment

Multi Channel Pipettor

Varied Pipettors

Shaker $CO_2$ Incubator

Biological Hood Type II

Plate reader

Press apparatus

TABLE 3

Product data sheet
PRODUCT: OWC - PSO - 1-2015
Psoriasis Cream
10% Cannabis (30%)
Date: 31 Oct. 2016
R&D: Ester

| % | T (° C.) | PLACEBO INGREDIENTS | GR | SAMPLE Nr. 2 | Notes |
|---|---|---|---|---|---|
| 58.820 | 80 | WATER | 588.200 | 0.58820 | |
| 11.000 | | ARLACEL 165 | 110.000 | 0.11000 | |
| 10.000 | | MYRITOL 318 | 100.000 | 0.10000 | |
| 5.000 | | GLYCERIN | | | |
| 5.000 | | CETYL ALCOHOL | 50.000 | 0.05000 | |
| 3.000 | | NIACINAMIDE PC | 30.000 | 0.03000 | |
| 1.700 | | SALICYCLIC ACID | 17.000 | 0.01700 | |
| 1.000 | | ALLANTOIN | 10.000 | 0.01000 | |
| 1.000 | | SHEA BUTTER | 10.000 | | |
| 1.000 | | VASELIN | | | |
| 0.500 | | BRIJ 721 | 5.000 | 0.00500 | |
| 0.500 | | VITAMIN E ACETATE | 5.000 | 0.00500 | |
| 0.500 | | LAVENDAR OIL | 5.000 | 0.00500 | |
| 0.200 | | RHODICARE D | 2.000 | 0.00200 | |
| 0.200 | | DERMACURE DG | 2.000 | 0.00200 | |
| 0.200 | | ALOE VERA GEL | 2.000 | 0.00200 | |

TABLE 3-continued

Product data sheet
PRODUCT: OWC - PSO - 1-2015
Psoriasis Cream
10% *Cannabis* (30%)
Date: 31 Oct. 2016
R&D: Ester

| | | | |
|---|---|---|---|
| 0.180 | TEA | 1.800 | 0.00180 |
| 0.100 | BISABOLOL | 1.000 | 0.00100 |
| 0.050 | DISODIUM EDTA | 0.500 | 0.00050 |
| 0.050 | BHT | 0.500 | 0.00050 |
| * | β-Caryophyllene | | |
| | p.H = 3.5-4.0 | | |
| 41.180 | | 1000.00 | 1.00000 |
| 100.000 | | 940.000 | 0.94000 |

| NOTES LABORATORY: | SILVERSON HOMOGENIZER DATE NET WT. | |
|---|---|---|
| PACKING: | PH: | VISCOSITY: |
| | SIGN: | STABILITY: |
| | DATE: | COLOUR: |

Definitions

In this experiment:

The term "topical formulation" or "cream formulation" refers hereinafter to the formulation described in Table 1 and/or to the formulation described in Table 3 which further contains *Cannabis* oil 3% THC:3% CBD.

The term "base formulation" or "placebo" or "vehicle formulation" refers hereinafter to the formulation presented in Table 1 without the cannabis oil and without the β-Caryophyllene 0.5%; and/or to the formulation presented in Table 3 without the β-Caryophyllene 0.5%.

The term "on site" refers hereinafter to a formulation prepared by mixing the "base formulation" or "placebo" or "vehicle formulation" with selected ingredient or combination of ingredients in order to test their effect or potential synergistic effect. For example: Test item on site:

Test item on site CBD:THC 3%:3% oil of Table 6 below means placebo formulation+cannabis oil 3%:3% THC:CBD (mixed "on site") (without β-Caryophyllene 0.5%).

Test Procedures

Human skins were obtained from healthy female (age 48-65) undergone abdominal plastic surgery. The study was initiated at the day of surgery.

Phase A: Dose Response Analysis

The assay was carried out in triplicates.

Fixed size of explant skin pieces (0.64 cm2) were cut from the skin tissue, using a designated press apparatus.

The skin pieces were prepared and maintained in air liquid interphase; the explants were laid in 6-well culture plates containing skin culture medium (DMEM supplemented with 100 U/ml penicillin and 100 μg/ml streptomycin), dermal side down in the medium and epidermis up. The pieces were left to recover at 37° C. with 5% $CO_2$ for 24 hr.

To induce inflammation characteristics, fresh culture medium was supplemented with LPS (10 μg/ml) and EGF (2.5 ng/ml), which were added to the appropriate wells, according to Table 4.

Culture medium without supplements was used as negative, unstimulated control (Group 1). In addition, ethanol was used as vehicle control Group (Group 2).

The stimulated control (Group 6) contained LPS, without addition of other agents.

10% SDS was used as positive control (viability reduction; Group 9).

Naïve and LPS-stimulated cultures were treated without or with six concentrations of three extracts by applying them on the epidermis topically (3 μl).

The active ingredients (THC, CBD or their equal combination-based herbs), eluted from the plants by EtOH, were used.

The extracts were diluted in EtOH from a 20% stock solution to final concentrations of (1) 20% [undiluted], (2) 10%, (3) 5%, (4) 3%, (5) 1% and (6) 0.1% (i.e., final concentration of THC/CBD on skin). The extract of 20% THC and 20% CBD stock solution was diluted to final concentrations of (1) 20%, 20% [undiluted], (2) 10%, 10% (3) 5%, 5% (4) 3%, 3% (5) 1%, 1% and (6) 0.1%. 0.1%. The extracts were measured with and without stimulation (LPS/EGF).

Concomitantly, three concentrations of the topical formulation, base formulation and base formulation supplemented with 0.5% β-caryophyllene was applied topically to the skin explants at total of 2 mg per cm2 without or with LPS/EGF (Group 18-29).

The content of the active ingredients in the stock formulation was 3% THC and 3% CBD. The tested concentrations were (1) stock=100%, (2) 66% (2% THC and 2% CBD), (3) 33% (1% THC and 1% CBD), (4) the stock formulation was mixed with the base formulation supplemented with β-caryophyllene. Extract containing 3% THC and 3% CBD was added to the vehicle formulation (without β-caryophyllene) and was tested as well as two dilutions.

The skin explants were incubated for 48 hr at 37° C. with 5% CO2.

Each well contained one skin piece (three wells/treatment).

At the end of all incubations, the epidermis was peeled and its viability was measured by the MTT assay, according to SOP.

TABLE 4

Treatment Groups-Dose response

| Group | Test item Description | Concentration | LPS/EGF |
|---|---|---|---|
| 1. | Control naive cells | n/a | − |
| 2. | Vehicle control (EtOH) | n/a | − |
| 3. | Test items | Undiluted (20%) | − |
| 4. | (3 extracts) with and without | 1:2 (10%) | − |
| 5. | stimulation | 1:4 (5%) | − |
| 6. | | 1:6.7 (3%) | − |
| 7. | | 1:20 (1%) | − |
| 8. | | 1:200 (0.1%) | − |
| 9. | Positive control | 10% SDS | − |
| 10. | Stimulated control | n/a | + |
| 11. | Stimulated Vehicle control (EtOH) | n/a | + |
| 12. | Test items | Undiluted (20%) | + |
| 13. | (3 extracts) with | 1:2 (10%) | + |
| 14. | and without | 1:4 (5%) | + |
| | stimulation | 1:6.7 (3%) | + |
| 16. | | 1:20 (1%) | + |
| 17. | | 1:200 (0.1%) | + |
| 18. | Formulation base control (placebo) | | − |
| 19. | Formulation base control + β-caryophyllene | | − |
| 20. | Test item, formulated | Undiluted | − |
| 21. | | 1:1 prepared on site | − |
| 22. | | 1:3 prepared on site | − |
| 23. | | Undiluted, prepared on site | − |
| 24. | Formulation base control (placebo) | | + |
| 25. | Formulation base control + β-caryophyllene | prepared on site | + |
| 26. | Test item, formulated | Undiluted | + |
| 27. | | 1:1 prepared on site (CBD:THC 2%:2%) | + |
| 28. | | 1:3 prepared on site (CBD:THC 1%:1%) | + |
| 29. | | Undiluted, prepared on site (CBD:THC 3%:3%) | + |

Phase B: Anti-Inflammatory Evaluation

The second phase was initiated based on the obtained results of phase A. Selected experimental conditions and concentrations of the extracts were analyzed according to the following experimental protocols:

The assays were carried out in triplicates.

Fixed size of explant skin pieces (0.64 cm2) were cut from the skin tissue, using a designated press apparatus.

The skin pieces were prepared and maintained in air liquid interphase; the explants were laid in 6-well culture plates containing skin culture medium (DMEM supplemented with 100 U/ml penicillin and 100 μg/ml streptomycin), dermal side down in the medium and epidermis up. The pieces were left to recover at 37° C. with 5% $CO_2$ for 24 hr.

To induce inflammation characteristics, fresh culture medium was supplemented with LPS (10 μg/ml) and EGF (2.5 ng/ml), which was added to the appropriate wells, as presented in Table 5.

Culture medium without supplements was used as negative, unstimulated control. In addition, ethanol was used as vehicle control Group (Table 5).

The stimulated control contained LPS, without addition of other agents.

Dexamethasone (10 μM) was used as positive control.

LPS-stimulated cultures were also treated without or with different ratio of CBD:THC by applying them on the epidermis topically (3 μl).

Concomitantly, the topical formulation, base formulation control and base formulation supplemented with β-caryophyllene were applied topically to the skin explants at 2 mg/cm2 without or with LPS/EGF.

The skin explants were incubated for 48 hr or 72 hr (selected treatments) at 37° C. with 5% CO2.

Each well contained two skin pieces (three wells/treatment).

Epidermis Turnover Rate

The assay was performed according to kit's manufacturer instructions. Briefly:

During the final 4 hours of culture, BrdU was added to each well.

The tissue was fixed, permeabilized and the DNA was denatured by the kit's buffers.

BrdU monoclonal antibody was pipetted into the wells and allowed to bind for one hour.

Colorimetric evaluation of the turnover rate was recorded by ELISA reader.

In addition, epidermis viability was determined by MTT.

Inflammatory Markers

Cytokines quantification in the spent medium was analyzed by using specific ELISA kits for IL-6 and IL-8. Calibration curves were generated in duplicates.

Results

Phase A: Dose Response Analysis

The study was initiated by a dose-response analysis to monitor the maximal concentration tolerated by the tissue.

Reference is now made to FIGS. 1A-1D illustrating a dose-response analysis, where the different Test items were applied topically without or with LPS/EGF. After 48 hr incubation, epidermis viability was determined by MTT. Mean±SEM, n=3.

FIGS. 1A-1D show the results on the CBD (FIG. 1A), THC (FIG. 1B), combination (1:1 ratio) (FIG. 1C) and topically applied formulation (FIG. 1D) without or with LPS/EGF stimuli. As expected, a mild increase in the viability was monitored when the skin explants were treated with LPS/EGF. In addition, although the vehicle (EtOH) did not impact the skin, the lowest concentration of CBD, THC and combination increased the MTT values. A possible pro-proliferative agent may be present in the extracts that mask an opposite effect of active compounds, and it is eluted differentially in ethanol.

The topical formulation had also an attenuating effect, affected only in the LPS/EGF-stimulated groups when compared to the placebo formulation.

The conclusion of this experiment was that there is no effect on cell cytotoxicity by any concentration of THC, CBD or their combination and that all concentrations are safe to use for further detection.

Phase B: Anti-Inflammatory Evaluation

The efficacy of the Test items on LPS/EGF-induced increase in epidermal turnover rate and cytokine secretion was evaluated. In view of the results obtained in the previous section, the treatment groups, concentrations and application duration were adjusted according to Table 5. In addition, epidermal viability was performed (MTT assay).

TABLE 5

Treatment Groups-Anti inflammatory evaluation

| Group/Test item | Test item Description | Concentration | LPS/EGF | Exposure time (hr) |
|---|---|---|---|---|
| 1. | Control naive cells | n/a | − | 48 |
| 2. | Vehicle control (EtOH) | n/a | − | 48 |
| 3. | Control naive cells | n/a | + | 48 |
| 4. | Vehicle control (EtOH) | n/a | + | 48 |
| 5. | Positive control | Dexamethasone | + | 48 |
| 6. | THC:CBD 3:0 | | + | 48 |
| 7. | THC:CBD 3:1 | | + | 48 |
| 8. | THC:CBD 3:3 | Only ethanol based extracts were, tested after 48 hr and 72 h | + | 48, 72 |
| 9. | THC:CBD 0:3 | | + | 48 |
| 10. | THC:CBD 1:3 | | + | 48 |
| 11. | THC:CBD 1:0 | | + | 48 |
| 12. | THC:CBD 0:1 | | + | 48 |
| 13. | Placebo | | − | 48, 72 |
| 14. | Placebo + β-caryophyllene | | − | 48, 72 |
| 15. | Topical formulation | Final formulation containing β-caryophyllene, THC:CBD 3%:3% (oil), tested after 48 and 72 hr | + | 48, 72 |
| 16. | Test item (on site) | Base formulation + THC:CBD 3%:3% (Ethanol), tested after 48 and 72 hr | + | 48, 72 |
| 17. | Placebo | | + | 48, 72 |
| 18. | Placebo + β-caryophyllene | | + | 48, 72 |

Reference is now made to FIGS. 2A-2D, which shows the impact of the Test items on viability, turnover rate, IL-8 secretion and IL-6 secretion in these experimental conditions.

FIGS. 2A-2D illustrates the effect of the Test items on epidermal turnover. The different Test items were applied topically without or with LPS/EGF. After 48 hr (black columns) or 72 hr (gray columns) incubation, epidermis viability and turnover rate were determined by MTT and BrdU, respectively. Mean±SEM. n=3. */# $p<0.05$ for differences from control or LPS-stimulated group, respectively.

Figure 2A:
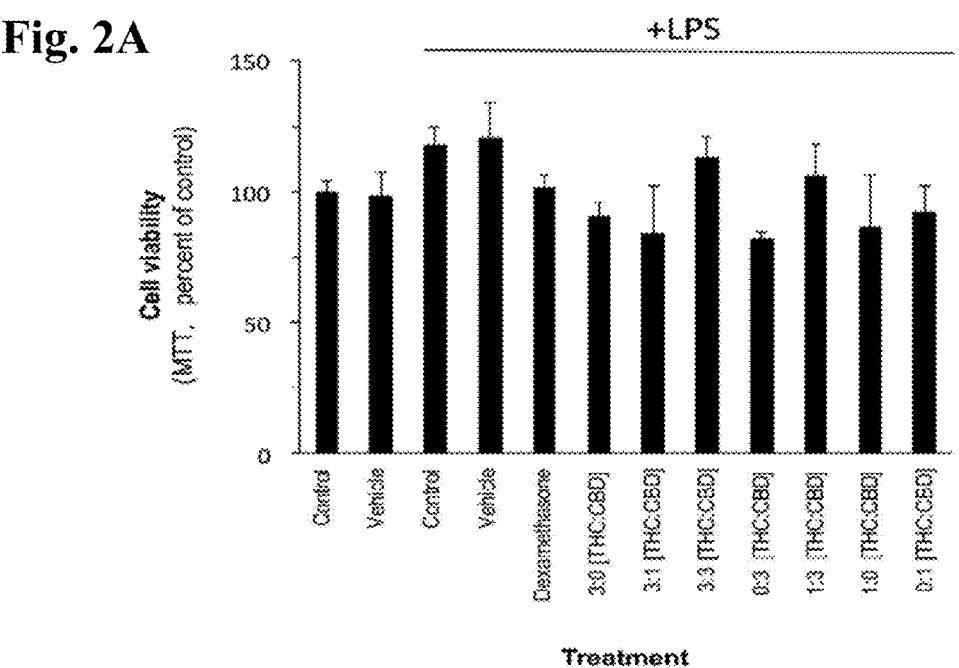
FIGS. 2A-D illustrate the effect of the Test items (Ethanol based extracts) on epidermal turnover: The different Test items were applied topically without or with LPS/EGF. After 48 hr (black) or 72 hr (gray) incubation, epidermis viability and turnover rate were determined by MTT (FIGS. 2A-2B) and BrdU (FIGS. 2C-2D), respectively. Mean±SEM. n=3. */# p<0.05 for differences from control or LPS-stimulated Test items, respectively.
Figure 2B:
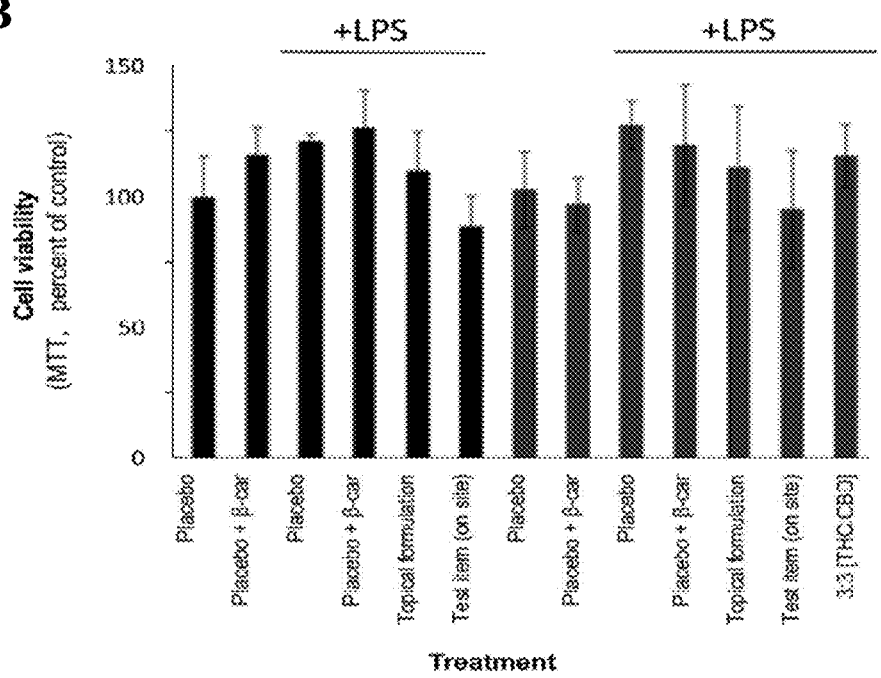

The results shown in FIGS. 2A and 2B show that the Test items were well tolerated by the skin explant even when exposed to the Test items for 72 hr.

Figure 2C:
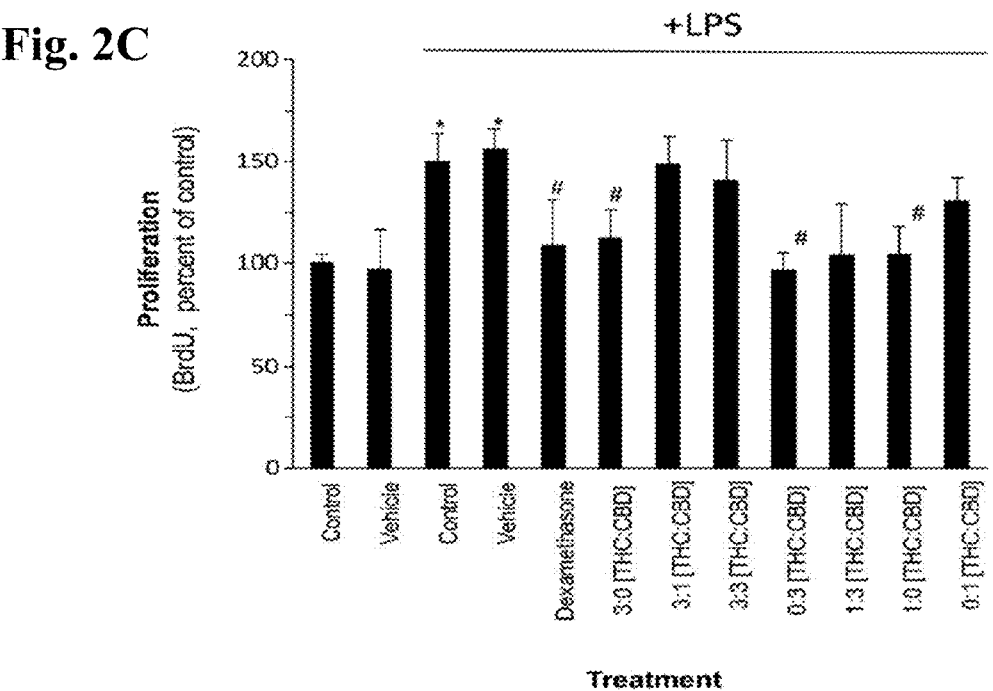
Figure 2D:
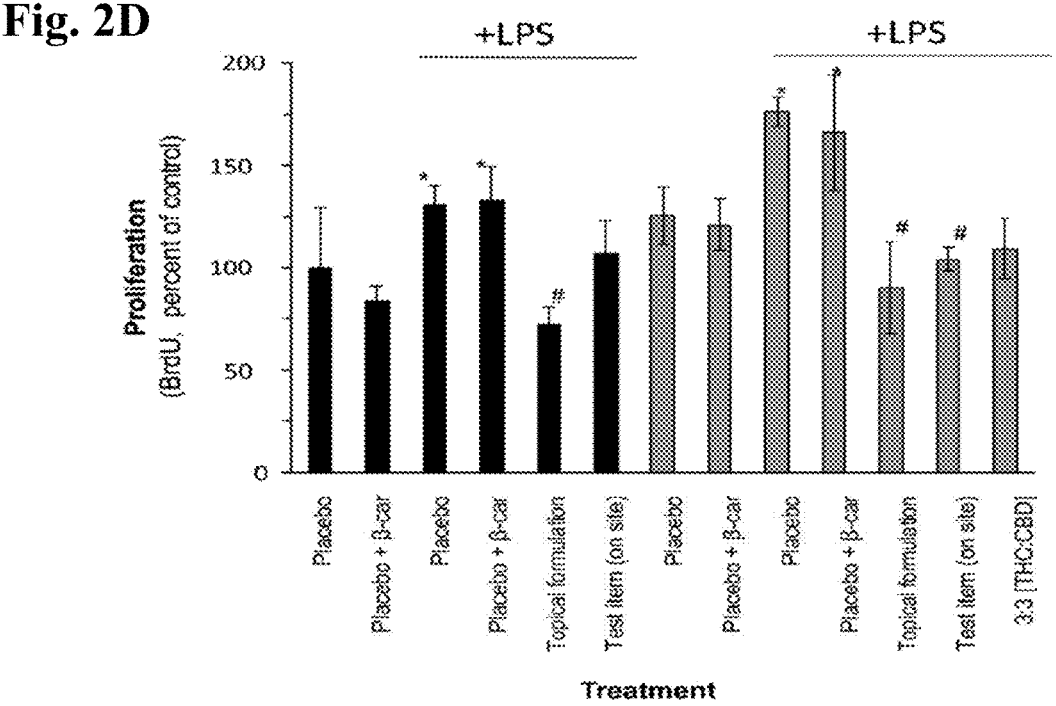

A significant effect was observed in the cells' turnover rate (FIGS. 2C and 2D). As expected, the inflamed environment increased the proliferating cell population by ~50%. Dexamethasone, the positive anti-inflammatory control, was able to completely block this enhancement.

Importantly, both CBD and THC alone at 3% (ethanol extracts, test items 9 and 6 respectively of Table 5) and the topical formulation (test item 15 of Table 5) showed significant reduction of the hyperproliferation caused by the LPS/EGF treatment in a comparable manner to the steroid control. The effect of the topical formulation was observed in both time points tested (48 and 72 hr). Interestingly, the combination of THC:CBD 3%:3% and also placebo with or without beta-caryophyllene (Test items 17 and 18 of Table 5) didn't show any significant effect on cell proliferation, but their combination (exhibited as Test item "on site" 16 of Table 5, and also topical formulation, Test item 15 of Table 5), showed a significant synergistic effect on cell proliferation.

Phase C: Oil *Cannabis* Extracts

In view of the results above, the effect of oil CBD, THC and combined extracts was determined in similar conditions (see Table 6).

TABLE 6

Treatment Groups (Test items)

| Group/Test item | Test item Description | Comments | LPS/EGF |
|---|---|---|---|
| 1. | Control naive cells | − | − |
| 2. | Vehicle control (oil) | − | − |
| 3. | Ethanol | − | − |
| 4. | Positive control | 10% SDS | − |
| 5. | Positive control | Dexamethasone | + |
| 6. | Control naive cells | − | + |
| 7. | Vehicle control (oil) | − | + |
| 8. | Ethanol | − | + |
| 9. | Positive control | Dexamethasone | + |
| 10. | THC 3% oil | − | + |
| 11. | CBD 3% oil | − | + |
| 12. | THC:CBD (3%:3%) oil | − | + |
| 13. | THC:CBD Ethanol | − | + |
| 14. | Placebo | − | − |
| 15. | Placebo + 0.5% beta care | − | − |
| 16. | Placebo | − | + |
| 17. | Placebo + 0.5% beta caryophyllene | − | + |
| 18. | Test item on site: THC 3% oil | prepared on site | + |
| 19. | Test item on site: CBD 3% oil | prepared on site | + |
| 20. | Test item on site: CBD:THC 3%:3% oil | prepared on site | + |
| 21. | Test item on site: CBD:THC 3%:3% Ethanol | | + |
| 22. | Topical formulation | | + |

Figure 3A:
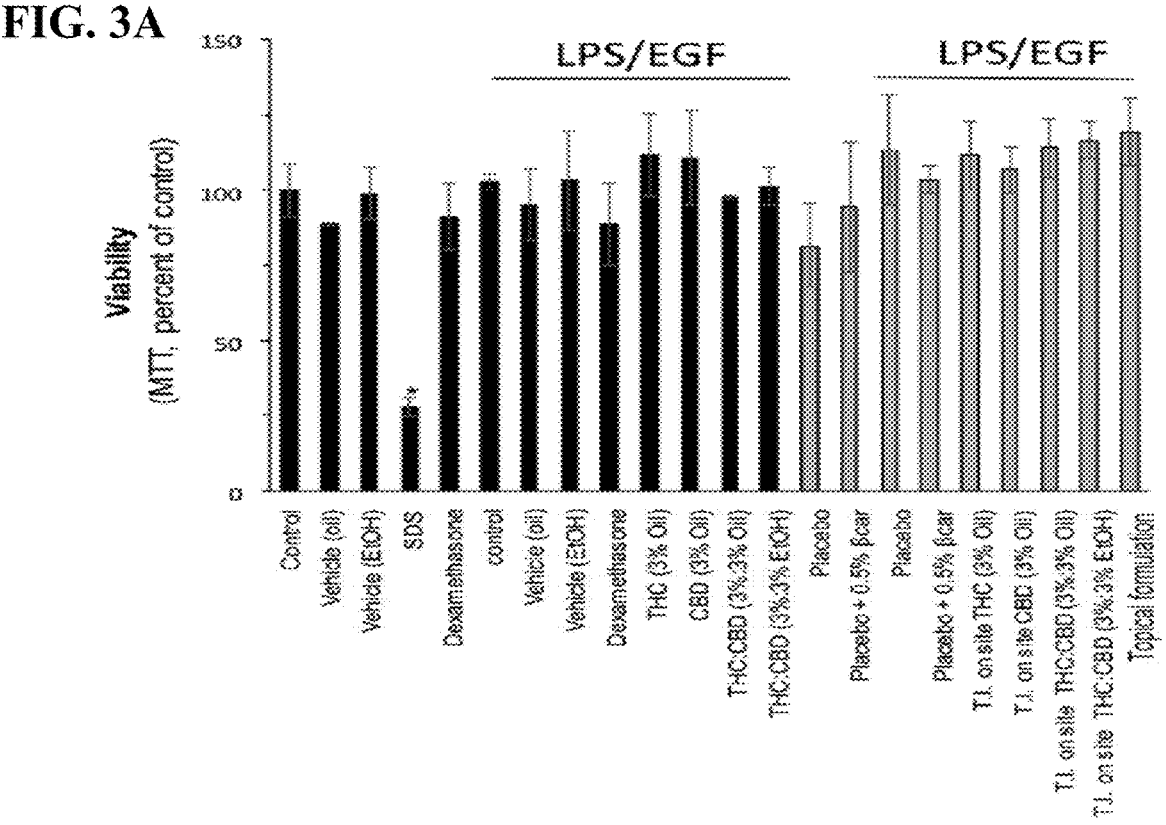
FIGS. 3A-3B illustrate the effect of the Test item (oil based extracts) on epidermal turnover. The different Test items were applied topically without or with LPS/EGF. After 48 hr, epidermis viability (FIG. 3A) and turnover rate (FIG. 3B) were determined by MTT and BrdU, respectively. Mean±SEM. n=3. */# p<0.05 for difference from control or LPS-stimulated Test item, respectively.
Figure 3B:
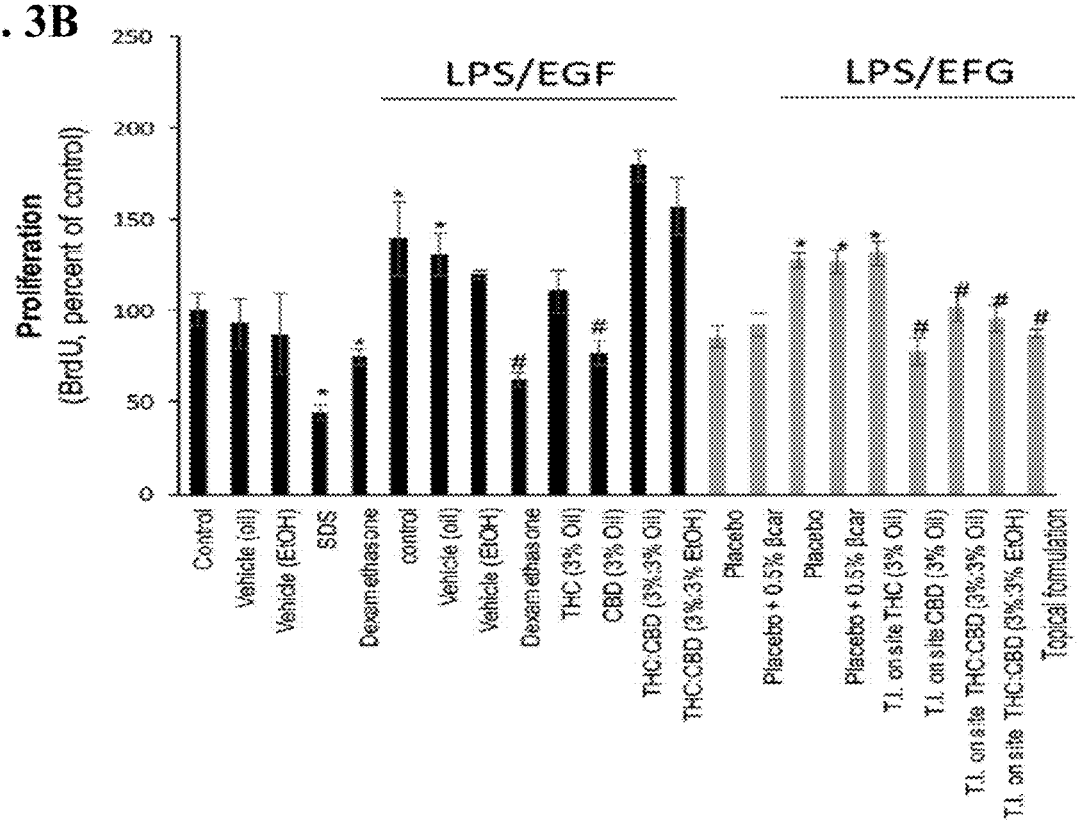

Reference is now made to FIGS. 3A-3B illustrating the effect of the Test items presented in Table 6 on epidermal turnover. The different Test items were applied topically without or with LPS/EGF. After 48 hr, epidermis viability (FIG. 3A) and turnover rate (FIG. 3B) were determined by MTT and BrdU, respectively. Mean±SEM. n=3 */# $p<0.05$ for differences from control or LPS-stimulated group, respectively.

FIGS. 3A-3B shows that the oil extracts were well tolerated by the skin tissues in the concentration tested.

Importantly, the CBD extract (Test item 11 of Table 6) attenuated LPS/EFG-induced hyperproliferation in a comparable manner to dexamethasone.

In addition, the *Cannabis* extract integrated on site into the placebo formulation (see Table 6: on site 3% THC oil, Test item 18; on site 3% CBD, Test item 19; on site CBD:THC 3%:3%, both oil and ethanol extracts, Test items 20 and 21, respectively; and the topical formulation Test item 22) showed significant anti-proliferative action. As showed with the ethanol extracts (see FIG. 2), the same synergistic effect was obtained with the formulation containing oil extracts. In other words, while the combination of THC:CBD 3%:3% (Test item 12 of Table 6) and also the placebo with or without beta-caryophyllene (Test items 16 and 17, respectively of Table 6) didn't provide any significant effect on cell proliferation, their combination, exhibited as the topical formulation (Test item 22 of Table 6) or the "on site" prepared formulations containing CBD:THC 3%:3% (Test items 20 and 21 of Table 6), demonstrated a significant synergistic effect on inhibition of cell proliferation.

The hypothesis that the Test items could attenuate cytokine secretion in an alternative model system was also evaluated. Thus, inflammation was induced by TNFα.

Figure 4A:
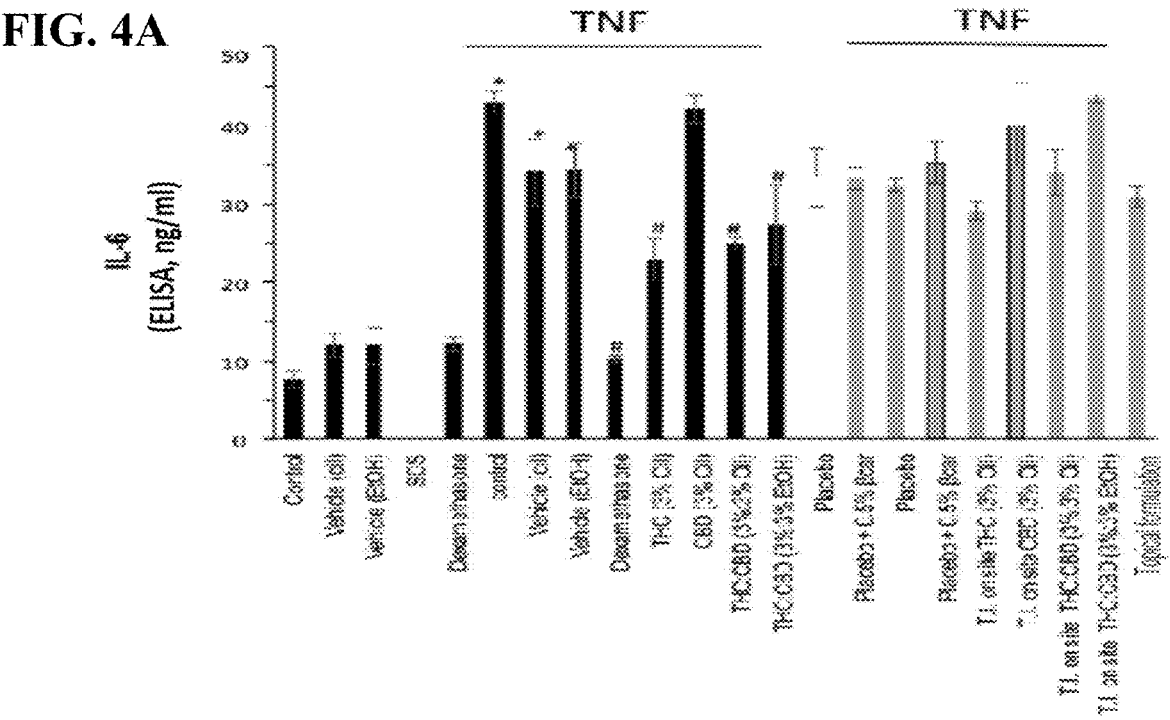
FIGS. 4A-4B illustrate the effect of the Test item (oil based extracts) on cytokine secretion. The different Test items were applied topically without or with LPS/EGF, as described in FIGS. 3A-3B. After 48 hr, IL-6 (FIG. 4A) and IL-8 (FIG. 4B) in the culture media were determined by ELISA. Mean±SEM. n=3. */# p<0.05 for differences from control or LPS-stimulated Test item, respectively.
Figure 4B:
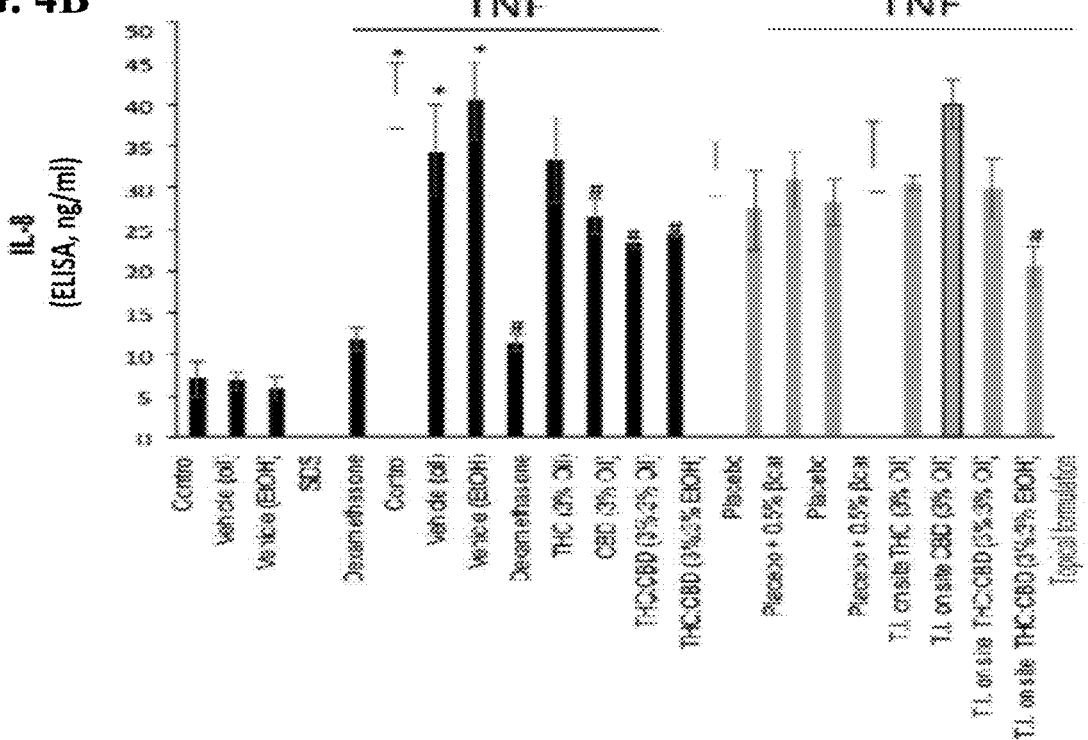

Reference is now made to FIGS. 4A-4B illustrating the effect of the oil extracts Test items of Table 6 on cytokine secretion. The different Test items were applied topically without or with LPS/EGF, as described in FIGS. 3A-3B. After 48 hr, IL-6 (FIG. 4A) and IL-8 (FIG. 4B) in the culture media were determined by ELISA. Mean±SEM. n=3. */# $p<0.05$ for differences from control or LPS-stimulated group, respectively.

The secretion levels of IL-6 and Il-8 are presented in FIGS. 4A-4B. It is noted that the vehicle control group (oil) (Test item 7 of Table 6) showed an effect and was not accurate. Thus, all relevant groups were compared to the respective naïve controls.

A significant impact was observed in the THC 3% oil (Test item 10 of Table 6) and THC:CBD oil and ethanol extracts (Test items 12 and 13, respectively of Table 6) on IL-6. CBD 3% oil (Test item 11 of Table 6), THC:CBD oil and ethanol extracts (Test items 12 and 13, respectively of Table 6) and the topical formulation (Test item 22 of Table 6) showed an effect on IL-8.

Figure 5:
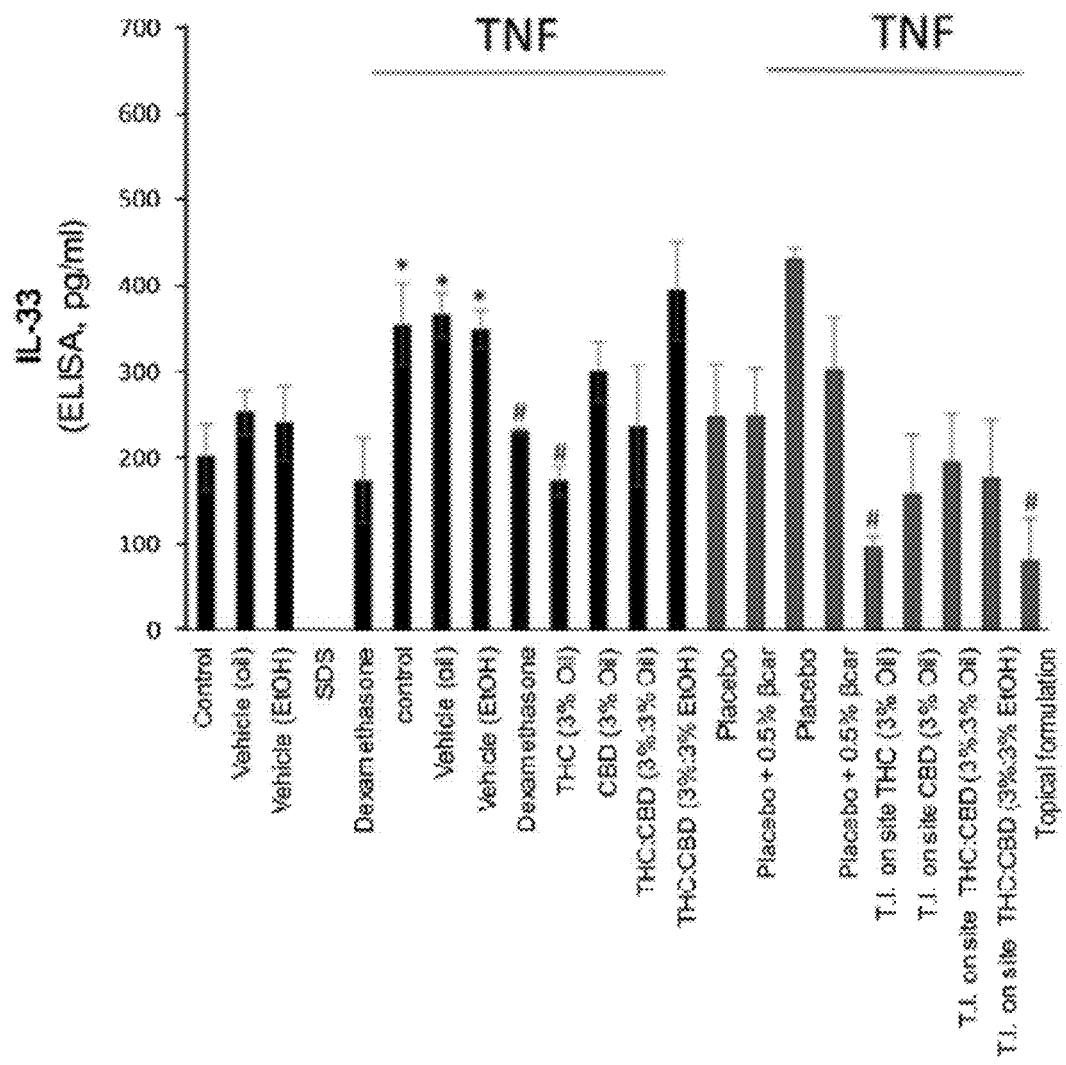
FIG. 5 illustrates the effect of the Test item (oil based extracts) on cytokine secretion. The different Test items were applied topically without or with LPS/EGF, as described in FIG. 3. After 48 hr, IL-33 in the culture media were determined by ELISA. Mean±SEM. n=3. */# p<0.05 for differences from control or LPS-stimulated Test item, respectively.

Reference is now made to FIG. 5 illustrating the effect of the Test items (oil extracts) on cytokine secretion. The different Test items were applied topically without or with LPS/EGF, as described in FIG. 3. After 48 hr IL-33 in the culture media was determined by ELISA. Mean±SEM. n=3. */# $p<0.05$ for differences from control or LPS-stimulated group, respectively.

FIG. 5 shows the results obtained for IL-33.

FIG. 5 shows a significant ameliorating effect of THC 3% oil (Test item 10 of Table 6), THC combined with the vehicle formulation (THC on site, Test item 18 of Table 6) and significant effect of the topical formulation (Test item 22 of Table 6). Interestingly, a synergistic effect was shown with the formulation containing oil extracts. While the combination of THC:CBD 3%:3% (Test item 20 of Table 6) and also placebo with or without beta-caryophyllene (Test items 16 and 17, respectively of Table 6) didn't have any significant on cell proliferation, their combination (the topical formulation, Test item 22 of Table 6) showed a significant synergistic effect on inhibition of cell proliferation.

Discussion and Conclusions

The study objective was to evaluate the effect of CBD, THC and combined extracts on skin inflammation.

The human skin organ culture was used as the experimental platform. Skin inflammation was induced by LPS/EGF or by TNFα.

Two psoriasis markers were evaluated: the increase in the epidermal turnover rate and the inflammation exhibited as the secretion of cytokines.

The results show that the topical formulation (containing CBD:THC 3%:3%) was well tolerated by the tissue and that it attenuated LPS/EFG induced hyperproliferation.

The results surprisingly show a synergistic effect on reducing proliferation, which is showed with both formulations containing oil and ethanol extracts. It is demonstrated that while the combination of THC:CBD 3%:3% and also placebo with or without beta-caryophyllene didn't show any significant effect on cell proliferation, their combination, presented as the topical formulation and/or test item on site, showed a significant synergistic effect on inhibition of cell proliferation.

In addition to its clear anti-hyperproliferative effect, the topical formulation of the present invention attenuated both IL-8 and IL-33 secretion.

A synergistic effect was also shown on IL-33 inhibition. While no effect was shown by the cannabis extracts THC:CBD 3:3 (Test item 12 of Table 6) or by the vehicle formulation (Test items 16 and 17 of Table 6), a significant effect was observed by the topical formulation (Test item 22 of Table 6).

As no effect was shown by the Test item on site THC:CBD 3:3 that doesn't contain beta-caryophyllene (Test item 20 of Table 6) on IL-8 and IL-33 inhibition, while a major inhibitory effect was shown by topical formulation (Test item 22), it is possible that beta-caryophyllene has also a synergistic effect with the base formulation.

To conclude, the results of this study clearly show that the topical formulation was well tolerated by the skin explants and demonstrated high potency against hyperproliferative and inflammatory conditions. An anti-proliferative and anti-inflammatory synergistic effect was observed by the topical formulation of the present invention as compared to the effect provided by THC, CBD extracts or their combination and by the topical formulation absent of cannabis extract and beta-caryophyllene.

Example 3

Anti-Inflammatory Evaluation of *Cannabis*-Based Extracts and Topical Formulations on Skin Morphology and Epidermal Turnover Rate Objectives In this study, the effect on skin morphology and epidermal turnover rate were monitored by histology.

Materials and Methods

Materials List—see Table 7 below.

TABLE 7

Material List

| No./ Name | Manufacturer/ Supplier | Cat No./ Lot No. | Physical State/ Storage Conditions | Expiry Date | Name in the report |
|---|---|---|---|---|---|
| Test Items | | | | | |
| 1. Test item 1 | Bazelet OWC | OWC 1.3 THC/CBD OWC 36217 | Liquid RT | n/a | Ethanol 3%:3% |
| 2. Test item 2 | Bazelet OWC | OWC 1:1 THC/CBD 17191 | Liquid RT | n/a | Oil 3%:3% |
| 3. Test item 3 | Bazelet OWC | OWC 2 THC 27191 | Liquid RT | n/a | Oil 3% THC |
| 4. Test item, formulated* | Bazelet OWC | OWC 3 CBD 37191 | Liquid RT | n/a | Oil 3% CBD |
| 5. Psoriasis cream* placebo | OWC OWC | PSO-1-2015 N/A | TBD TBD | n/a | Test item, formulated |
| 6. Test item 4 | OWC OWC | OWC-PSO-1- placebo (2) | Formulation RT | n/a | Placebo formulation |

TABLE 7-continued

Material List

| No./ Name | Manu-facturer/ Supplier | Cat No./ Lot No. | Physical State/ Storage Con-ditions | Expiry Date | Name in the report |
|---|---|---|---|---|---|
| Skin culture medium | | | | | |
| 7. DMEM | Biological Industries | 01-052-1A | Liquid | 10/17 | DMEM |
| | Biological Industries | 1643856 | 2-8° C. | | |
| 8. Penicillin-streptomycin solution | Biological Industries | 03-033-1B | Frozen | 1/18 | Pen Strep |
| | Biological Industries | 1628553 | (−25)-(−15)° C. | | |
| Other reagents | | | | | |
| 9. PBS | Biological Industries | 02-023-1A | Liquid | 11/17 | PBS |

*For product data sheet see Table 3

Formulations:

All formulations were done under sterile conditions.

Skin Culture Medium:

DMEM was supplemented with 100 U/ml penicillin and 100 μg/ml streptomycin, filtered.

LPS (10 μg/ml):

Stock (1 mg/ml): 10 mg of lyophilized LPS was reconstituted in 10 ml PBS, aliquoted and stored at −20° C. The stock was diluted 1:100 in culture medium to reach a final concentration of 10 μg/ml.

EGF (2.5 ng/ml):

Stock (200 μg/mL): 100 μg of lyophilized EGF was reconstituted in 0.5 mL PBS, aliquoted and stored at −20° C. The stock was diluted in a stepwise manner 1:20 and then 1:4000 in skin culture medium to reach a final concentration of 2.5 ng/ml.

Test Item:

Unless written otherwise, the Test items and vehicle formulation were received sterile and ready to use in their final concentration. All materials were kept in reduced light and humidity conditions at RT.

Please note that the Test item "on site" preparation was performed by constant stirring of the placebo formulation with the indicated amount of extracts for 10 min. at RT.

Disposal of Materials

The disposal of samples will be carried out by the test facility. The samples are placed into a bio hazard bag and disposed into the central bio hazard container.

General Equipment

Multi Channel Pipettor

Varied Pipettors

Shaker $CO_2$ Incubator

Biological Hood Type II

Plate reader

Press apparatus

Test Procedures

Human skins were obtained from healthy female (age 48-65) that underwent abdominal plastic surgery. The study was initiated at the day of surgery.

Phase A: Dose Response Analysis

The assay was carried out in triplicates (for cytokines) and one sample for histology.

Fixed size of explant skin pieces (0.64 cm2) were cut from the skin tissue, using a designated press apparatus.

The skin pieces were prepared and maintained in air liquid interphase; the explants were laid in 6-well culture plates containing skin culture medium (DMEM supplemented with 100 U/ml penicillin and 100 μg/ml streptomycin), dermal side down in the medium and epidermis up. The pieces were left to recover at 37° C. with 5% CO2 for 24 hr.

To induce inflammation characteristics, fresh culture medium was supplemented with LPS (10 μg/ml) and EGF (2.5 ng/ml), which were added to the appropriate wells, according to Table 8.

Culture medium without supplements was used as negative, unstimulated control (Group 1). In addition, ethanol and oil were used as vehicle control Group (Groups 2 & 3).

The stimulated control (Group 6) contained LPS/EGF, without addition of other agents.

10% SDS was used as positive control (viability reduction; Group 9).

LPS-stimulated cultures were treated without or with the extracted tested items by applying them on the epidermis topically (3 μl), as presented in Table 8.

The extracts (CBD, THC and 1:1 mixture) were tested at 3%.

The active ingredients (CBD, THC or their equal combination-based herbs), eluted from the plants, were used.

Concomitantly, the extracts were integrated on site with the placebo formulation supplemented with β-caryophyllene and tested, along with a pre-prepared 3%:3% CBD:THC topical formulation (Group 22).

Histological Evaluation:

The skin explants were incubated for 48 hr at 37° C. with 5% CO2.

Each well contained one skin piece.

At the end of all incubations, the skin samples were washed with PBS (*3) and fixed in 4% formaldehyde at RT for 2 hr.

The samples were washed three more times with PBS, and were kept in 70% ethanol at 2-8° C. overnight. The ethanol was replenished and all samples were kept in similar condition until used.

Samples were transferred into histological cassettes and processed for the dehydration and paraffin embedding, according to the standard protocol.

Paraffin blocks were prepared and sectioned at 5 micrometers. Sections were mounted onto standard histological glass slides (2 sections per slide) and stained with hematoxylin-eosin, or Ki67 staining.

TABLE 8

Treatment Groups-Dose-response

| Group/Test item | Test item Description | Comments | LPS/ EGF |
|---|---|---|---|
| 1. | Control naive cells | − | − |
| 2. | Vehicle control (oil) | − | − |
| 3. | Ethanol | − | − |
| 4. | Positive control (10% SDS) | Not analyzed, for internal control only | − |
| 5. | Positive control | Dexamethasone | − |
| 6. | Control naive cells | − | + |
| 7. | Vehicle control (oil) | − | + |
| 8. | Ethanol | − | + |
| 9. | Positive control | Dexamethasone | + |
| 10. | THC 3% oil | − | + |
| 11. | CBD 3% oil | − | + |
| 12. | THC:CBD (3%:3%) oil | − | + |
| 13. | THC:CBD Ethanol | − | + |

TABLE 8-continued

Treatment Groups-Dose-response

| Group/Test item | Test item Description | Comments | LPS/EGF |
|---|---|---|---|
| 14. | Placebo | − | − |
| 15. | Placebo + 0.5% beta-care | − | − |
| 16. | Placebo | − | + |
| 17. | Placebo + 0.5% beta caryophyllene | − | + |
| 18. | Test item on site: THC 3% oil | prepared on site | + |
| 19. | Test item on site: CBD 3% oil | prepared on site | + |
| 20. | Test item on site: CBD:THC 3%:3% oil | prepared on site | + |
| 21. | Test item on site: CBD:THC 3%:3% Ethanol | | + |
| 22. | Topical formulation | | + |

Results

Histological Evaluation

To ascertain the effect of the Test item on inflammation-induced hyperproliferation and skin morphology, histological examination was performed.

Figure 6:
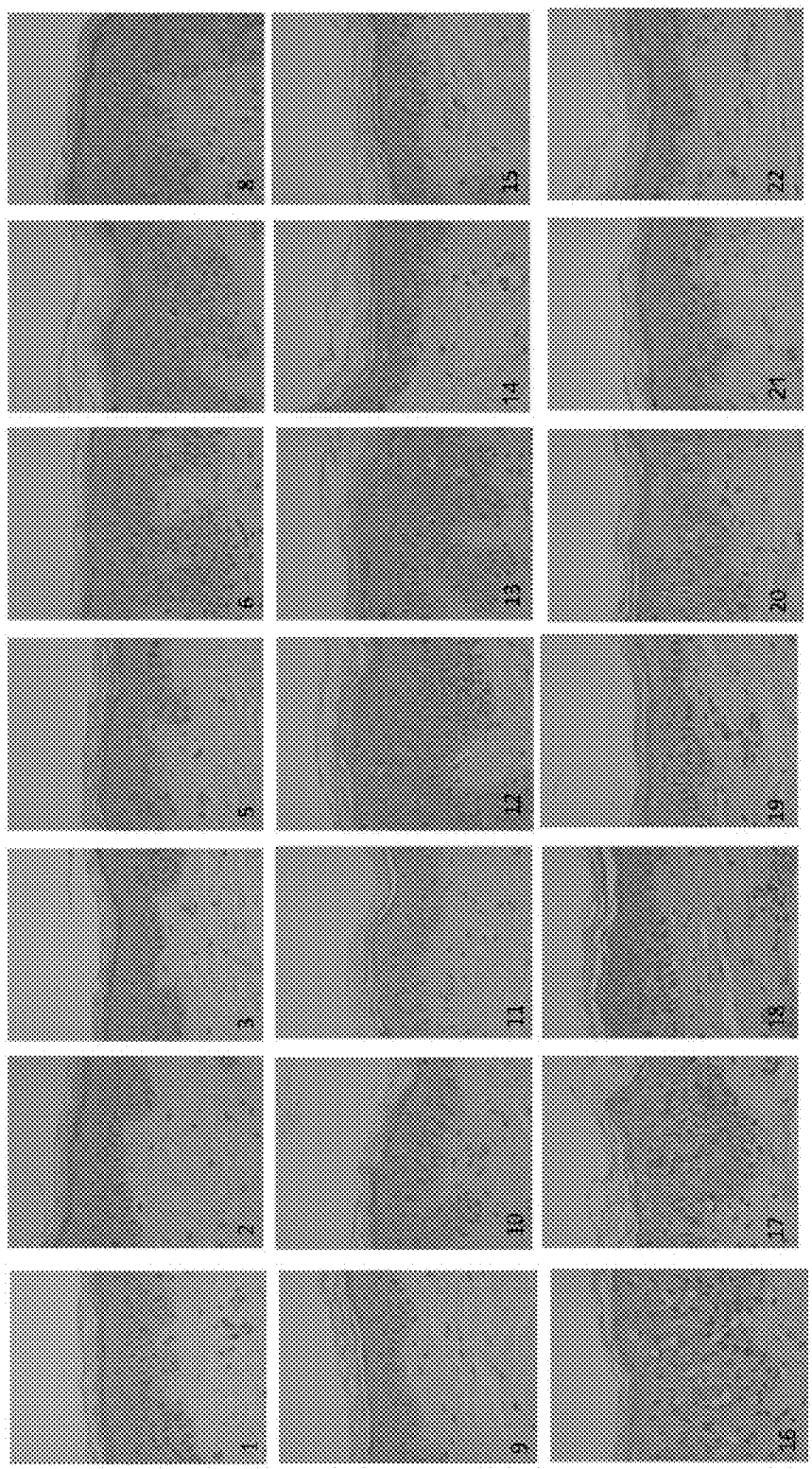
FIG. 6 illustrates representative images of histological examination by H&E (Hematoxylin and eosin) stain. Selected Test items were applied topically without or with LPS/EGF, fixed and were taken to histological examination.

Reference is now made to FIG. 6 illustrating representative images of histological H&E (Hematoxylin and eosin) stain. Selected Test items were applied topically without or with LPS/EGF, fixed and taken to histological examination.

Figure 7:
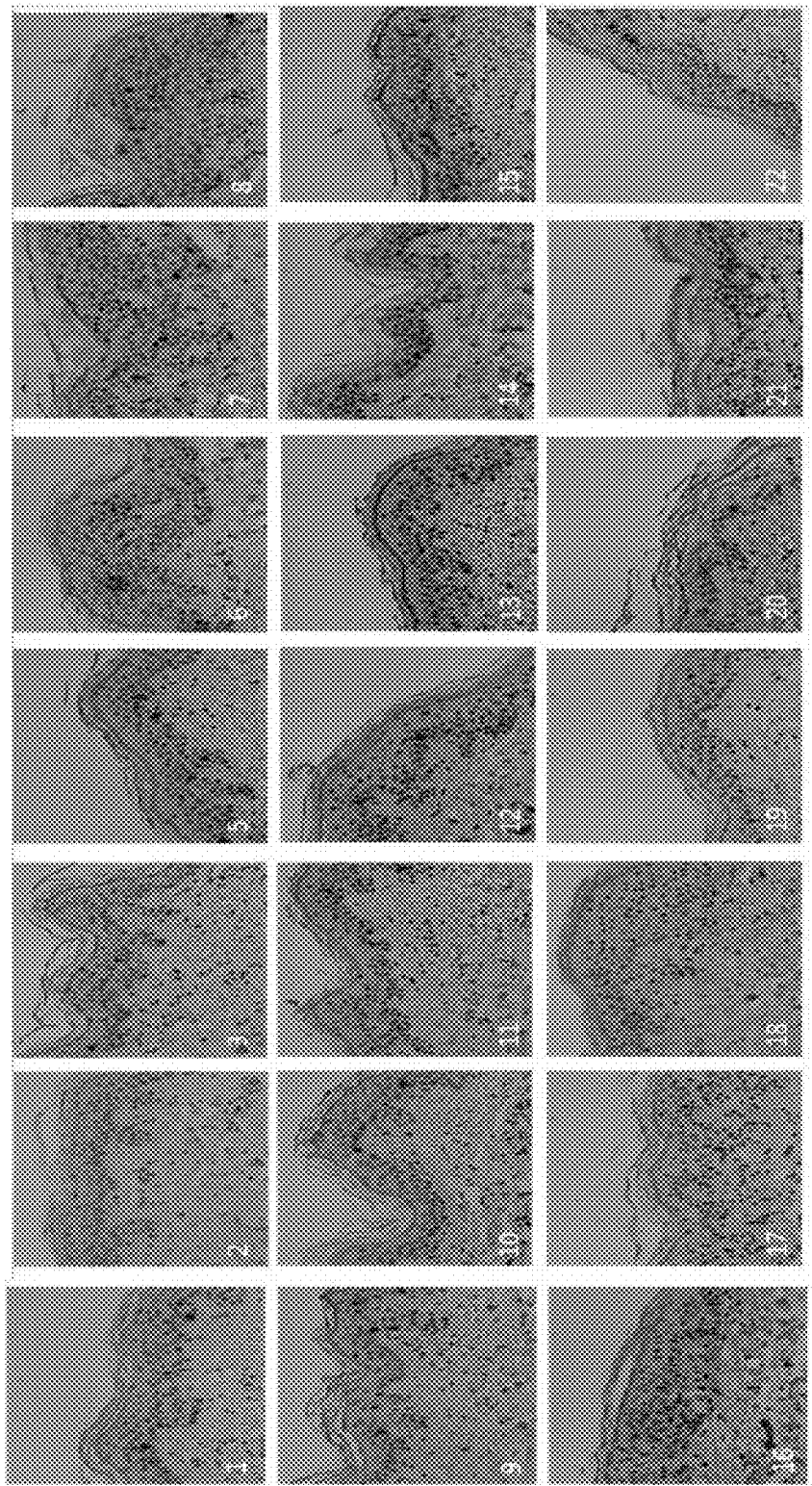
FIG. 7 illustrates representative images of histological examination by Ki67 staining. Selected Test items were applied topically without or with LPS/EGF, fixed and taken to histological examination.

Reference is now made to FIG. 7 illustrating representative images of histological examination by Ki67 staining. Selected Test items were applied topically without or with LPS/EGF, fixed and taken to histological examination.

As expected, LPS/EGF treatment increased inflammation characteristics of the skin; both Acanthosis and hyperproliferation were observed (FIG. 6 and FIG. 7).

In addition, the vehicles (EtOH and oil) did not show any effect on the skin morphology or proliferative stages.

Importantly, the 3% CBD extract (Test item 11 of Table 8) was able to attenuate the inflammation phenomena in a comparable manner to the positive control group (Dexamethasone). A moderated effect was also observed in the THC treated group (Test item 10 of Table 8).

The effect of CBD and THC was also noticeable when integrated in the placebo cream formulation (Test items 20, 21 of Table 8).

In addition, the topical formulation (Group 22 of Table 8) had also an attenuating activity, when compared to the placebo formulation supplemented with β-caryophyllene (Test item 17 of Table 8). This effect was comparable to those obtained by the corticosteroid positive control (Test item 9 of Table 8).

The synergistic effect was shown in this experiment as well. While no effect was shown when treated with THC:CBD 3:3 (Test item 12 of Table 8) and not when treated with placebo with or without beta-caryophyllene (Test items 16 and 17, respectively of Table 8), a significant effect was shown when treated with the topical formulation (Test item 22 of Table 8).

Discussion and Conclusions

The study objective was to evaluate the impact of CBD, THC and combined extracts and formulations on skin hyperproliferation.

The human skin organ culture was used as the experimental platform. Skin hyperproliferation and inflammation was induced by LPS/EGF.

In line with the experiments described in Example 2, the hyperproliferation of the epidermal tissue under the inflamed environment was attenuated by 3% CBD and by the topical formulation. A moderated effect was shown in the THC treated group.

This data is comparable to those obtained by the BrdU data of Example 2.

The results described in Example 2 show that some of the Test items (CBD, THC or their combination) and mainly the topical formulation, attenuated TNFα-induced inflammation. Without wishing to be bound by theory it is submitted that the compounds may be affecting the signal cascade mediated by TNF.

To conclude, the results of this study clearly show that the topical formulation of the present invention demonstrates high potency against hyperproliferative and inflammatory conditions.

Example 4

A Protocol for a Double-Blind, Placebo-Controlled, Randomized Study for Assessing the Effect of the Composition of the Present Invention Comprising THC, CBD or Derivatives or Combinations Thereof on Relieving Psoriasis Symptoms Objectives:

To assess the effect of Tetrahydrocannabinol (THC), Cannabidiol (CBD) and derivatives and combinations thereof in relieving psoriasis symptoms.

Study Design:

This example provides a double-blind, placebo-controlled, randomized study.

The study population includes patients suffering from psoriasis which are treated in the dermatology department of a hospital.

The effect on psoriasis symptoms is assessed by using the Psoriasis Area and Severity Index (PASI) in patients self-administering up to about 30 mg of an active ingredient selected from the group consisting of: THC, CBD, β-Caryophyllene and any combination thereof per day, or about 4 topical applications per day of Cannabis oil containing composition cream (e.g. as presented in Table 8).

Study Population:

The study population includes patients presenting with chief complaint of psoriasis of moderate to severe degree.

Primary Outcome Measure: incidence and risk factors for serious adverse events and adverse effects.

Secondary Outcome Measure:

Assessing changes in symptoms using the Psoriasis Area and Severity Index (PASI), Number of Subjects:

Up to 100 subjects in two groups (up to 50 subjects each).

Maximal Study Duration Time:

Up to 7 visits in up to 23 weeks as follows:

Screening phase—up to 3 weeks, 1 visit

Treatment phase—16 weeks, 4 visits

Follow-up phase—4 weeks, 2 visits

Study Design:

Prospective, double-blind, placebo-controlled, randomized, outpatient study assesses the efficacy of Medical Grade Cannabis (MGC) in subjects suffering from psoriasis, for up to 16 treatment weeks and additional 4 follow-up weeks in up to 100 subjects.

Inclusion Criteria:
Individuals eligible to be enrolled into this protocol are participants who:
1. 18-65 years old
2. Meet criteria for psoriasis. Differential diagnosis is negative.
3. Are willing to commit to medication dosing and to complete evaluation instruments and study visits.
4. Agree not to change the type or increase the frequency of current psychotherapy, if any, nor change therapists (if they are concurrently seeing an outside therapist).
5. Agree not to change the identity or increase the dosage or frequency of use of pharmacotherapy for treatment of psoriasis.
6. If female participants of childbearing potential, must be willing to have pregnancy tests and must agree to use an effective form of birth control.
7. Agree not to participate in any other interventional clinical trials during the study.

Exclusion Criteria:
Individuals not eligible to be enrolled into this protocol are those who:
1. Are pregnant or nursing, or of child bearing potential and not practicing an effective means of birth control.
2. Have evidence of significant, uncontrolled hematological, endocrine, cerebrovascular, cardiovascular, coronary, pulmonary, gastrointestinal, or neurological disease. (Participants with hypothyroidism who are on adequate and stable thyroid replacement will not be excluded).
3. Have any allergies to marijuana.
4. Are not able to give adequate informed consent.
5. Have used marijuana within a month of starting the study.
6. Fail the initial urine drug screen and blood test which tests for illicit drug use within the prior month.

Sample Size:
Up to 100 subjects

Statistical Analysis:
Descriptive statistics is calculated for all data.

Results:
It appears from the results of the above described clinical study that in comparison to the placebo control, the cannabis oil composition of the present invention (i.e. cream formulation), comprising essentially THC or combinations of THC and CBD, positively affected psoriasis symptoms.

It is demonstrated that patients administered with the cannabis composition of the present invention, in a therapeutically effective dosage and according to a predetermined protocol, showed an improvement in psoriasis symptoms as measured by PASI (i.e. reduction of at least one PASI score) used for assessing changes in psoriasis severity.

The invention claimed is:
1. A method of treating or inhibiting an inflammatory skin disease in a human in need thereof comprising topically administering to the human a therapeutically effective amount of a pharmaceutical composition comprising:
   a. a carrier formulation comprising β-caryophyllene, salicylic acid, and at least at least one of:
      i. glycerin; or
      ii. niacinamide; and
   b. cannabis oil comprising cannabidiol and tetrahydrocannabinol, wherein the inflammatory skin disease is selected from the group consisting of spongiotic dermatitides, psoriasiform dermatitides, interface dermatitides, bullous disease, dermatitides with perivascular inflammation, vasculitis, nodular and diffuse dermatitides, seborrheic dermatitis, lupus erythematosus, discoid lupus erythematosus, dermatomyositis, lichen planus, lichen sclerosus, lichen simplex chronicus, psoriasis, lichen striatus, lichen aureus, granuloma faciale, atopic dermatitis, sweet syndrome, granuloma inguinale, pyoderma gangrenosum, necrobiotic xanthogranuloma, pemphigus, pemphigus foliaceus, pemphigus vulgaris, dermatitis herpetiformis, erythema multiforme, follicular occlusion triad, ruptured cyst/follicle, cutaneous T-cells lymphoma, poison ivy, nummular dermatitis, and eczema.

2. The method of claim 1, wherein the cannabidiol:tetrahydrocannabinol concentrations ratio in the cannabis oil is 1%:1%, 3%:1%, 1%:3%, or 3%:3% by weight.

3. The method of claim 1, wherein the pharmaceutical composition comprises:
   a. a carrier formulation comprising:
      i. glyceryl stearate and PEG-100 stearate;
      ii. glycerin;
      iii. niacinamide;
      iv. cetyl alcohol;
      v. salicylic acid;
      vi. allantoin;
      vii. butyrospermum parkii;
      viii. petrolatum;
      ix. steareth-21;
      x. tocopheryl acetate;
      xi. lavandula angustifolia oil;
      xii. xanthan gum;
      xiii. dipotassium glycyrrhizate;
      xiv. aloe barbadensis leaf juice;
      xv. triethanolamine;
      xvi. bisabolol;
      xvii. disodium EDTA; and
      xviii. β-caryophyllene; and
   b. *cannabis* oil comprising cannabidiol and tetrahydrocannabinol in a 1:1 ratio.

4. The method of claim 1, wherein the concentration of cannabidiol and tetrahydrocannabinol each is 3% by weight, and the concentration of said β-caryophyllene is 0.5% by weight.

5. The method of claim 1, wherein the topically administered pharmaceutical composition provides a synergistic effect with respect to treatment of the inflammatory skin disease as compared to the effect provided by administering the carrier formulation or the cannabis oil, each alone.

6. The method of claim 5, wherein the synergistic effect provided is with respect to at least one of: (a) inhibition of proliferation; (b) inhibition of inflammation; and (c) inhibition of epidermal turnover rate.

7. The method of claim 6, wherein the synergistic effect is with respect to inhibition of proinflammatory cytokines secretion.

8. The method of claim 7, wherein the cytokines are IL-8, IL-33 or any combination thereof.

9. The method of claim 1, wherein the topically administered pharmaceutical composition provides a synergistic effect with respect to reduction of hyperproliferation, reduction of IL-8 secretion, reduction of IL-33 secretion, reduction of skin inflammation, reduction of epidermal turnover rate, and any combination thereof, as compared to the effect provided by administering the carrier formulation or the cannabis oil, each alone.

10. The method of claim 1, wherein the topically administered pharmaceutical composition provides a synergistic effect with respect to inhibition of skin hyperproliferation and skin inflammation as compared to the effect provided by each component of the carrier formulation (a) when administered separately in a similar concentration.

11. The method of claim 1, wherein the pharmaceutical composition is formulated in a dosage form selected from the group consisting of cream, ointment, lotion, foam, film, transdermal patch and any combination thereof.

12. The method of claim 1, further comprising administration of at least one additional therapeutic agent selected from the group consisting of methotrexate, cyclosporine, hydroxycarbamide, fumarates, retinoids, efalizumab and alefacept, vitamin D and derivatives thereof, and any combination thereof.

13. The method of claim 12, wherein the administration of at least one additional therapeutic agent is in combination with the topically administered pharmaceutical composition so as to provide a synergistic or additive effect with respect to treating or preventing the inflammatory skin disease relative to the effect provided by the therapeutic agent administered separately.

14. The method of claim 1, wherein the pharmaceutical composition is formulated for administration in a therapeutic dosage selected from the group consisting of:
   a. a dosage of up to about 1500 mg per day;
   b. a dosage in the range of from about 100 mg to about 1500 mg per day;
   c. a dosage comprising an amount of up to about 30 mg each of cannabidiol or tetrahydrocannabinol or both, and an amount of up to about 5 mg $\beta$-caryophyllene, administered once, twice or thrice daily;
   d. a dosage comprising an amount of cannabidiol of up to about 30 mg per day, about up to 100 mg per day, or in the range of from about 10 mg to about 100 mg per day;
   e. a dosage comprising an amount of tetrahydrocannabinol of up to about 30 mg per day, about up to 100 mg per day, or in the range of from about 10 mg to about 100 mg per day; and
   f. a dosage comprising an amount of $\beta$-caryophyllene of up to about 5 mg per day, up to about 100 mg per day, or in the range of from about 3 mg to about 10 mg per day.

15. The method of claim 1, wherein the amount of cannabis oil in the pharmaceutical composition is about 10% by weight.

16. The method of claim 1, wherein the inflammatory skin disease is psoriasis.

17. The method of claim 16, wherein the topically administered pharmaceutical composition provides a synergistic effect with respect to treating symptoms of psoriasis including thickened, dry, scaly, flaky, cracked, itchy, red and or inflamed skin.

* * * * *